(12) United States Patent
Styrkarsdottir et al.

(10) Patent No.: US 6,630,304 B1
(45) Date of Patent: Oct. 7, 2003

(54) HUMAN OSTEOPOROSIS GENE

(75) Inventors: Unnur Styrkarsdottir, Reykjavik (IS); Vala Drofn Johannsdottir, Reykjavik (IS)

(73) Assignee: deCODE genetics ehf., Reykjavik (IS)

( * ) Notice: Subject to any disclaimer, the term of this patent is extended or adjusted under 35 U.S.C. 154(b) by 0 days.

(21) Appl. No.: 09/661,887

(22) Filed: Sep. 14, 2000

(51) Int. Cl.⁷ .......................... C12Q 1/68; C07H 19/00
(52) U.S. Cl. ........................................ 435/6; 536/23.5
(58) Field of Search .............................. 435/6; 536/23.5

(56) References Cited

U.S. PATENT DOCUMENTS

| | | |
|---|---|---|
| 5,266,683 A | 11/1993 | Oppermann et al. |
| 5,863,758 A | 1/1999 | Oppermann et al. |

FOREIGN PATENT DOCUMENTS

| | | |
|---|---|---|
| WO | WO 99/57261 | 11/1999 |
| WO | WO 00/04183 | 1/2000 |

OTHER PUBLICATIONS

Sambrook et al in Molecular Cloning, 1989, Cold Spring Harbor Laboratory, CSH, NY, Ch. 11 & 17.*
Wallace et al in Methods Enzymol 152: 432–439, 1987.*
Dale, L. and C.M. Jones, "BMP Signalling in Early Xenopus Development", *Bioessays, 21*(9):751–760 (1999).
Zimmerman, L.B., et al., "The Spemann Organizer Signal Noggin Binds and Inactivates Bone Morphogenetic Protein 4", *Cell, 86*(4):599–606 (1996).
Krisch, T., et al., "Crystal Structure of the BMP–2–BRIA Ectodomain Complex", *Nature Structural Biology, 7*(6):492–496 (2000).
Massague, J., "TGF–β Signal Transduction", *Annu. Rev. Biochem., 67*:753–791 (1998).
Aspenberg, P., et al., "The Bone Morphogenetic Proteins Antagonist Noggin Inhibits Membranous Ossification", *J. Bone Miner Res., 16*(3):497–500 (2001).
Chen, D., et al., "Bone morphorgenetic protein 2 (BMP–2) enhances BMP–3, BMP–4, and bone cell differentiation marker gene expression during the induction of mineralized bone matrix formation in cultures of fetal rat calvarial osteoblasts.", *Calcif. Tissue Int., 60*:283–90 (1997).
Chen, D., et al., "Differential roles for bone morphogenetic protein (BMP) receptor type IB and IA in differentiation and specification of mesenchymal precursor cells to osteoblast and adipocyte lineages.",*J. Cell Biol., 142*:295–305 (1997).
Fujii, M., et al., "Roles of bone morphogenetic protein type I receptors and Smad proteins in osteoblast and chondroblast differentiation." *Mol. Biol. Cell, 10*:3801–13 (1999).

Miyazono, K., "Signal transduction by bone morphogenetic protein receptors: functional roles of Smad proteins." *Bone, 25*:91–3 (1999).
Takazawa, Y., et al., "An osteogenesis–related transcription factor, core–binding factor A1, is constitutively expressed in the chondrocytic cell line TC6, and its expression is upregulated by bone morphogenetic protein–2." *J. Endocrinol., 165*:579–586 (2000).
Thirunavukkarasu, K., et al., "The osteoblast–specific transcription factor Cbfal regulates the expression of osteoprotegerin (OPG), a potent inhibitor of osteoclast differentiation and function.", *J. Biol. Chem., 275*(33):25163–25172 (2000).
Thompson, D.B., et al., "Linkage between stature and a region on chromosome and analysis of a candidate gene, bone morphogenetic protein 2.", *Am. J. Med. Genet., 59*:495–500 (1995).
Sugiura, T., "Cloning and functional characterization of the 5'–flanking region of the human bone morphogenetic protein–2 gene.", *Biochem. J., 338*:433–40 (1999).
Wang, E.A., "Bone morphogenetic proteins (BMPs): therapeutic potential in healing bony defects." *Trends Biotechnol., 11*:379–83 (1993).
Wozney, J.M., et al., "Novel regulators of bone formation: molecular clones and activities." *Science, 242*:1528–34 (1988).
Christiansen, M., et al., "CBFA1 and topoisomerase I mRNA levels decline during cellular aging of human trabecular osteoblasts," *J Gerntol A. Biol. Sci. Med. Sci., 55* (4): B194–200 (2000).
GenBank Seq. AL035668, Mar. 2001.
Helvering, L.M., et al., "Regulation of the Promoters for the Human Bone Morphogenetic Protein 2 and 4 Genes", *Gene, 256*:123–138 (2000).
Birren, B. et al., "Homo sapienschromosome 14, clone RP11–19605," [online] Accession No. ac026511, Mar. 2000. Retrieved from EMBL Database.
Thompson, D.B. et al., "Linkage Between Stature and a Region on Chromosome 20 and Analysis of a Candidate Gene, Bone Morphogenetic Protein 2," *Am. J. of Med. Genet. 59*:595–500 (1995).

* cited by examiner

*Primary Examiner*—Christina Chan
*Assistant Examiner*—Phuong N. Huynh
(74) *Attorney, Agent, or Firm*—Hamilton, Brook, Smith & Reynolds, P.C.

(57) ABSTRACT

A role of the human BMP2 gene in osteoporosis is disclosed. Methods for diagnosis, prediction of clinical course and treatment for osteoporosis using polymorphisms in the BMP2 gene are also disclosed.

9 Claims, No Drawings

SEQUENCE LISTING

<160> NUMBER OF SEQ ID NOS: 2

<210> SEQ ID NO 1
<211> LENGTH: 14759
<212> TYPE: DNA
<213> ORGANISM: Homo sapien
<220> FEATURE:
<221> NAME/KEY: CDS
<222> LOCATION: (3639)...(3984)
<221> NAME/KEY: CDS
<222> LOCATION: (11757)...(12601)

<400> SEQUENCE: 1

| | | | | | |
|---|---|---|---|---|---|
| ccttggtttt | ggggatcatt | tgggcaagcc | cgaggtgctg | tgcatggggg | ctcctggaat | 60 |
| cctgggaagg | gcagaaagcc | ttggccccag | actcatcgtg | cagcagctct | gagcagtatt | 120 |
| tcggctgagg | agtgacttca | gtgaatattc | agctgaggag | tgacttggcc | acgtgtcaca | 180 |
| gccctacttc | ttgggggcct | ggtggaagag | ggtggcgtag | aaggttccaa | ggtcccaaac | 240 |
| tggaattgtc | ctgtatgctt | ggttcacaca | gtgcgttatt | ttaccttcct | ctgagctgct | 300 |
| aatcgcctgc | ctctgagctg | ggtgagataa | atatcacaag | gcacaaagtg | attgtacaat | 360 |
| aaaaaaatca | aatccctccc | atccatcctt | cagtctgcca | cacacgcagt | ctacgttaca | 420 |
| cacatgtcac | gtaaagcagg | atgacatcca | tgtcacatac | atagacatat | taaccgaaat | 480 |
| gtggcccttc | ggttgcatat | attctcatac | atgaatatat | ttatagaaat | atatgcacat | 540 |
| attttttgtat | attggatata | tttatgtaac | tataaattta | catgcgtatg | gatatgaaaa | 600 |
| taaatgcata | cacatttatg | taaaaaaatt | tgtacacatg | catttacata | tgtaaataca | 660 |
| tacatctcta | tgtattaatg | tttaaaaaca | ctcaatttcc | agcctgctgt | tttcttttaa | 720 |
| ttttcctcct | attccgggga | aacagaagcg | tggatcccac | gtctatgcta | tgccaaaata | 780 |
| cgctgtaatt | gaggtgtttt | gttttgtttt | gtttttttgaa | atcgtatatt | accgaaaaac | 840 |
| ttcaaactga | aagttgaata | acgggcccag | cggggaaata | agaggccaga | ccctgaccct | 900 |
| gcatttgtcc | tggatttcgc | ctccagagtc | ccgcgaggg | tccggcgcgc | cagctgatct | 960 |
| ctcctttgag | agcagggagt | ggaggcgcga | gcgcccccct | tggcggccgc | gcgcccccgc | 1020 |
| cctccgcccc | acccgccgc | ggctgccgg | gcgcgccgtc | cacaccctg | cgcgcagctc | 1080 |
| ccgcccgctc | ggggatcccc | ggcgagccgc | gccgcgaagg | gggaggtgtt | cggccgcggc | 1140 |
| cgggagggag | ccggcaggcg | gcgtcccctt | taaaagccgc | gagcgccgcg | ccacggcgcc | 1200 |
| gccgccgccg | tcgccgccgc | cggagtcctc | gccccgccgc | gctgcgcccg | gctcgcgctg | 1260 |
| cgctagtcgc | tccgcttccc | acaccccgcc | ggggactggc | agccgccgcc | gcacatctgc | 1320 |
| cgccacagcc | tccgccggct | acccgaacgt | tctcggggcc | agcgccgagt | ggatcaccgg | 1380 |
| ggaccgcgag | gcaccgcgc | gccgcagacc | ccgcgcgggc | tggagcaccc | ggcagagcgc | 1440 |
| gccacagcgc | cgtggcctct | gctgcccggg | ctgcgccaga | gccgcggacg | ggcgcgcaga | 1500 |
| gcgccgggga | ctccggagcc | gatccctagc | gccgcgatgc | ggagcaccta | ctgcaggaga | 1560 |

-continued

```
tcggggcct gggacgcgct ggccgaggtg tgatcggacc ccaggctagc cacaaagggc      1620
acttggcccc agggctagga gagcgagggg agagcacagc cacccgcctc ggcggcccgg      1680
gactcggctc gactcgccgg agaatgcgcc cgaggacgac ggggcgccag agccgcggtg      1740
ctttcaactg gcgagcgcga atggggtgc actggagtaa ggcagagtga tgcgggggg       1800 caactcgcct ggcaccgaga tcgccgccgt gcccttccct ggacccggcg tcgcccagga      1860
tggctgcccc gagccatggg ccgcggcgga gctagcgcgg agcgcccgac cctcgacccc      1920
cgagtcccgg agcggcccc gcgcgggcc acgcgtccct cgggcgctgg ttcctaagga      1980
ggacgacagc accagcttct cctttctccc ttcccttccc tgccccgcac tcctccccct      2040
gctcgctgtt gttgtgtgtc agcacttggc tggggacttc ttgaacttgc agggagaata      2100
acttgcgcac cccactttgc gccggtgcct ttgccccagc ggagcctgct tcgccatctc      2160 cgagcccac cgcccctcca ctcctcggcc ttgcccgaca ctgagacgct gttcccagcg      2220
tgaaaagaga gactgcgcgg ccggcacccg ggagaaggag gaggcaaaga aaggaacgg      2280 acattcggtc cttgcgccag gtcctttgac cagagttttt ccatgtggac gctctttcaa      2340
tggacgtgtc cccgcgtgct tcttagacgg actgcggtct cctaaaggta gaggacgcgg      2400
gccagggccc ggggtgggtg gtgggtggga ggggatttg ggcagccact gcggtagagc      2460
ccttccttac gtccaggcca gaagtaaaca daccctctc cagtccacgt gcaacggagc      2520
cctgcagggg ctcccacttc cagctgcccc gggcgaccgt aagcctcacc ctcccggccc      2580
gcactcttcc accctctttt cttccctctc ccctggaata cttttggagc tgttaacact      2640
tagatgaggt gttttattta tttatttatt tattttttaat tttttttaaaa actttttttgg      2700 gtcaaagaaa tccctttgag agggtagccc ctgggtttca cccgttagct gagaacctgt      2760
ccgctctgcc atggtgatct ccattcttca agtgtttccg ggagacttgg tttctttgct      2820
cagagccgtg tcccatttag gaaagtacta ggagtttggg gttctcccta cttgtttcca      2880
gaaatgcgag gggtcagtac tgaaggatca cttggtactg tgttttaac agctgacacg      2940 tgcattaata gatattcacc atttacgtaa tcccgggaag atacatgtgt atcttgactg      3000
cactgtgggg atgcgggatg gagctgcctt tcgagacacc cctgagggta ggggcctggg      3060
acacaagtca taagtggctt cagaagttgt ggccttgagc ttacagggtc tggaagctat      3120
aagggtgtgt gtgtgtgtgt gtgtgtgtgt gtgtgtgtgt caggaagttc tatacagtgc      3180
ctctaaggaa gtcacatgca ccatttatgt gtgttatat gccagacagc gctcagcact      3240
ccgcatttgg gtttgtatag gggacgcagg gtgtcagatc aagcggtggt tttcccaggt      3300
tcccggcatt ggctgtcagc gctgtgtcac acacaaaaaa gtgacagtca ttggcgctgg      3360
tttggttggg gggagggca aatcccaaat ctgatgtcag acgagctaag cgttggatgg      3420
gagcgataaa tcatctggtt caggaacttg ggaccccttca ttatcccaaa cgtttgagct      3480
tcggtcggtc ttacctagac tcgtgagtgt gccaagccag gagggcatcc tggaggaggc      3540
acgccagcca aatgggagac cgggccgcgg gggcgcgagg ggggaggact gggcggggaa      3600
ctcgggtgac tcacgtcggt cctgtccgca ggtcgacc atg gtg gcc ggg acc cgc      3656
                                            Met Val Ala Gly Thr Arg
                                             1               5 tgt ctt cta gcg ttg ctg ctt ccc cag gtc ctc ctg ggc ggc gcg gct       3704
Cys Leu Leu Ala Leu Leu Leu Pro Gln Val Leu Leu Gly Gly Ala Ala
        10                  15                  20 ggc ctc gtt ccg gag ctg ggc cgc agg aag ttc gcg gcg gcg tcg tcg       3752
Gly Leu Val Pro Glu Leu Gly Arg Arg Lys Phe Ala Ala Ala Ser Ser
```

-continued

```
              25                  30                  35
ggc cgc ccc tca tcc cag ccc tct gac gag gtc ctg agc gag ttc gag    3800
Gly Arg Pro Ser Ser Gln Pro Ser Asp Glu Val Leu Ser Glu Phe Glu
         40                  45                  50 ttg cgg ctg ctc agc atg ttc ggc ctg aaa cag aga ccc acc ccc agc    3848
Leu Arg Leu Leu Ser Met Phe Gly Leu Lys Gln Arg Pro Thr Pro Ser
 55                  60                  65                  70 agg gac gcc gtg gtg ccc ccc tac atg cta gac ctg tat cgc agg cac    3896
Arg Asp Ala Val Val Pro Pro Tyr Met Leu Asp Leu Tyr Arg Arg His
                 75                  80                  85 tca ggt cag ccg ggc tca ccc gcc cca gac cac cgg ttg gag agg gca    3944
Ser Gly Gln Pro Gly Ser Pro Ala Pro Asp His Arg Leu Glu Arg Ala
             90                  95                 100 gcc agc cga gcc aac act gtg cgc agc ttc cac cat gaa g gtgaggcatg   3994
Ala Ser Arg Ala Asn Thr Val Arg Ser Phe His His Glu
        105                 110                 115 gagcagggcg tggggcggg gagtcaccct gcaaagccct ccaccgtggg cagactgcag    4054
ccgtccctgt agaggcagct tggccggggc accagcggac gtttccactc ttgcttctgt    4114
actatcgttt ctgaatctga ttttaactca ctgcttgtgt ggtggggag ccagggattc     4174 ccctttagta actccgcacc ctcttcctgg cttgcagcca aagagctac tcctcctgga     4234 agaattggag agaaatcaag tgatggggaa gatgagggca aaaggcatgc ctctagtcag    4294
ctaaacgtgc aagaattcca cagagggaaa aggagaaaaa gggaggcaga ttgagatttc    4354
tttaagtctg tttggaagct tttgctctat aaatctgccg cttaagccag ggttttaggg    4414
tagacagagc caagggcaga gttttcagag atagtattga aaaatcaaag cccagggccc    4474
caaagtcttt ctaatttata gttgatctgg gcctggtttg aagattttg aatcccaatc     4534 taatccccgt gggagatcaa tactacaatc aatcttattg tttccacaat gactttcttg    4594
tcctgtgctt aaatctgaga taggctctga gtagagacaa ggcaagcctt cagataaaag    4654
cgtttgtagc agctgcctgt tttttttca tgtgcaccga aatgtggatt ttttttctt     4714 ttatgatact acatgtggtt tttctaaggt gggatatttc tgcttgtttc atcagaaggg    4774
catttagtgg actggaaatg tcttacagca gctattgagg tctgctgtac ctaagttctt    4834
agagcaatta gtcaaaaata tgttccactt caattctttt tctacacttt taaatgcttc    4894
tttggcttaa tacatttaaa atagagcatg ggtttcttca attcctagaa aagagtacaa    4954
aagtgtatat cacagagcaa ccacttggca gatatttggg gagttgggag tgaagttctc    5014
tttcttgcct ttccctgctt aggtggtaaa tttcaagtgg gaaatttaca ctgataatag    5074
actaatggga aatggcactt ccagatgttt tctcccagtg tgaagggtga cttatacttg    5134
tgagagtatt tgttggtaat gggaataagt cccaaaggca agccacatag cagaagatac    5194
gttctcattg aggcagctac acattacgac ggggacactg aattgatcat cagttcattt    5254
acaagcacat ttctaagtga ggtgctctct gctagcagaa atcagatttg aaaggcagta    5314
agatctcact ccactctttc agaattcatc caatgaaagc agaaatcacc tgttgtcata    5374
tgtaaaattt gtgtgtatgt gtacattctg ccatcttaac cctgaaatga ttatagatcc    5434
agctaatcat tcccaggtaa tgctgattag aatactttt tttttgtata ggaatgtaat     5494
aagaacaact gttttagaca cctcttctgg aaatttgca tggaagctct caactttatt     5554
tttaaggcct ggaagatgct gtgtctctgt tacaacttaa aaggaagatc atttaagtta    5614
gttaacacct aaaacattcc attgtgtgag gatttttatca gtgatgtctg catattctca    5674
tcattcatct agaagtggtt tgatcagaac taaacaggct acacgttatt caactgtgtt    5734
```

```
atttaactt aaaaagcatg cttgagttta taaaatcaga atttatatct ttgtgagtgt    5794
aaatgttacc tgagaaacag tacagaagtg accaacttga ttaaaatcaa cttgtaataa    5854
cttcaggtct taatgcagtt agataatgga gaaaagctat gtaattttgc cccaaatttc    5914
aactaatcca tttcttgtct cattatgact aatatatcat ccttaatctg gatggatata    5974
gcactttttt caagactaat cattgttgta tacacccagg atttgctttt gataaacatc    6034
cttgtgccat gcatgccacg aaaaagttt ttggtaaacc atgtgatgaa ggttgctggc    6094
tcaagaacag aatttagttt ctacagcatt aatgagcatt tatttgaaaa aagaccataa    6154
agacccaatc ataagaatta cctgttgggt tttctttgta ggtgtgatcg aatggtttgg    6214
tggaattact cgacgagata tcatgatagc attctttcaa ccaatatgag tataatgcga    6274
ccatatcata gggatctga gacagaatta tcagttgtat ttttcctatt gaattttgtc    6334
tagtcctttc tccagtggct tttatttggg agaatatcag ctttgctaaa atgttattgt    6394
tttcaagatc attaaaaagt gcttcagcta catagacctt tggaaactgc cattgaacat    6454
agaaaagtca gttctgcaag tggaaagagt gttttgtgta ttgctgtagt tggaaacaca    6514
ttgaaactgg ttgacttcac tggccctcca aaaagtcttt atgcttttt gtcagatggg    6574 agagagaaag accaggtgct tcttgttctc ctcactctga aggacacagt cttctttcta    6634
catgaaataa ctggattatt tgcctctgtg actgaagctt caaatagag attaaccctc    6694 tttccacaaa tataattatt atgaaaatat ccatataata gaaagttca agaaataact    6754 attgccctgc attagagact ttgtggcaca aattcccccg tgcaaacaac agatttggac    6814
acatagatcc accaaaacca atacttacct ggtatggttc cctagtggcc ccaggtattt    6874
cattgtcatt acagaggcca cattaagtag gaaaattact ctatttggaa atggttgttg    6934
agattgaggc tttggtgtcc agtgatactt ccttggcact gacattttcc gttccacctg    6994
ttttttagtg gttcccctaa atttctctta atcctttgc agtgaactat tttgcgttct    7054
tagacttgct ctttgtgtat tttcactgag acaataagag aatatttcat cattccgaag    7114
gtgttggtgt taagggtggg cagaggccaa atcaggttg ttgatgacaa ccatgctctc    7174 tattcccttta tttgccattc ccttgttgta tttttttaa aatggaatgt ttttaacctt    7234
ttgtatttga tattttttt ctccttgatc agttgtctgt tattttatta tctggaaaat    7294
cttatattat actcagcctc tttcattttg tgttagggca gtgacttcca gccttactga    7354
ttgccagcat atccccaggt tttgttgttg ttgttgttgt tttactggag atttttagc    7414 ccaaagtgtg ttttaaaatc ctcgaagcat aacggtaact tacttttttg ataaaactta    7474
ccatacttta tttagaacaa aagggcagcc acaaaatagc agtggctcct tataaaatag    7534
acacattcca gtgggccccg tcacttttct gctcatttct gtctgttctg tccatcatac    7594
ctaagtcata tatttctgtt catttagttg ggacagaact cacccaatgt tatcattgta    7654
ctaaatataa atgtgcccct aatggttttg acttttgctt aagtttttga gtcctcatgt    7714
atgttaggta gtgccatcta gtagccagaa atttgggaac tggctgggca tgatggctaa    7774
tacctgtaat cccagcactt tgggaggctt aggtgggtgg atcacttgag gtcaggagtt    7834
ccagaccagc ctgccaaca tggtgaaacc acatctctac taaaatataa aaaaatagcc    7894
aggtatgatg gcccatgcct gtaatccgag ctaattggga ggctgagatg gaggactgc    7954 ttgaacctgg gaggtggagg ctgctgtgag ccaagattgt gccactgcac tccagcctgg    8014
gcaacagagt gagaccctgt gtcacaaaaa caagaaacaa aacaaaacaa aagacaagaa    8074
```

```
acctgagaag cgcagtagat tcaattatat atatctactt ttaatttgct agctctgtga   8134
ccttaggaaa gttacataac ctctctgaac tgcaactgtt tcatttacaa aatggagata   8194
atgatagttt ttctctaatt ggtttgttgt gagataattc atataaagct gatggtgcca   8254
gattacactc aaaaaaagca ttcagctgtc attatcatta tgacttcttt tgttaatgtt   8314
atagcctttc cttctctagg gaaaggagg ccagagtgga cctaggctga ctgagagaat    8374
tcagctcagt cttttgaatt attttgaggt agaggaatga ttgatatagt atagattatt   8434
aaattaggac ttcacttttg gagaaaagtt cagatatcat tgttgtctta tttttcttca   8494
ctttcccaca tttttgcagc catagctcca tccatttggt taagaactta gaagctcaca   8554
aactcgggtc aaagacaggt cgaaatcctc aaatccctta agaacttcag cttattcagg   8614
aagggatatt tacagaaaac tagcaattgt ataagtctcc aaaaaagcat acattacttg   8674
aggatccata tattttggc atcctcaggg ttgctgtgat gatttataga aggtttgttt    8734
atttaattta ctttatttca aataggtttt aattttgta cccttaagaa aagattcgta    8794
ctcttccctg gcagattaaa gaaaatgagc gtatattccc taaccttggc cagttacttt   8854
cctgggtttg agggtttctg tgaacgtcta acttacctct gtgacctgtt tctgcaacca   8914
ggggtgttgc aatggatgct tttgtcttga ggatgggacc tttcaagaaa cagattcact   8974
gaggtgcagt gggaaggtca gagaaagatc ttcgtatcgc ctattattat ttgctcgtct   9034
atttttctc ctttcttaag gccactaact gattctcctt tgctaaggct gcctacttcc    9094
actgagacct tgaaccacat gaaattgttg ttgtctgtgt ttctggtcaa atagtggcaa   9154
ttttgtatga ttcaatcttg tcatttaatt ttttgggagg ttattattct atttcatacc   9214
tttttttatac ccatcttctt tacttcattt acctgtccct catacttgac ttgtagcttg  9274
tcccttcact gtcatcgtct ggccatgtgg gtgtgtacgt gtgtgcgaga gagagaatgt   9334
gtgagaatgt atgtttcttt atgcattggg atttagggtt tttcttgcaa ttgtgatttc   9394
tctgggcact tttgttaata tagctagtca gcgagtgctc tagataattt ccttgcctc    9454
ccctctttg aaagaaaaga gggtgttctt agatgtattc ttatcagata agccagtagc    9514
tcaggtgctg gtctggcttt ggtgtcattg gggtctgagg ttgctgactt ttaccttctc   9574
tgctgaaaaa ttaccttcag cagaaacgtc tgaattgcaa ggagaaggag aaaaaaacag   9634
gccaaacaca gtccttggta ctccttggga gccactgaga agagtccagg ttcaaatggt   9694
cagaaggtta ttttaatgat tgtgtctggc ctaaagtacc attagcttcc agtgagtttt   9754
agaatgtgga tggatcctga aaggtattcc ccagaggttt ggattaatag gcacaaggga   9814
accctaaagg actctattgg cctgatactc cccatatcca cgtagaagag ctttagaaga   9874
accttctgtt ctgagaccct ggctgggccc acccagagct ggcccattca actcttactc   9934
ctttgccacc actaatggtt cttctactag ttttttatatt atttaacaaa aaggcacttt  9994
aaaaatgcac tcctggcaat ctatactgga atatgaaaaa catgctgcaa aaccttgaca  10054
ctccaagtgt ggtcttacag ttcccagaat cccctccttg aggagctgct agaaatgctg  10114
aatctcaagc atctccccag acctactgaa tcagagcctg catctgaagc tttacggtgt  10174
acaagctgtt ttatgtgaag gctgaagttt gaaaagcact gcattaaagc gttagtttgg  10234
tataaactgc cctgactgaa cttggtgtgt ccacttagct tgcatgatga ctgttgcttt  10294
gatgatgaag gctacacgg gtagatcctt tgagtgagtg atctgacatg attctccttt   10354
gctaaggcat ctagattcag tgcacaactt acagctgttt gtctttaggg gaaatacaac  10414
tgtaaaatta ataaaaacat agtctcttct tatgataaca tggaacgatg gcaaaataga  10474
```

```
ttttgttagc acttgggtag gaattctgaa tgaagcaggc aaattctgtt ggcagtgaaa      10534
tgataggatg tggtaaagtt agaataaaat aaacttaaat gtctcaaact ctcatggtat      10594
atactaccag tttaataata atgttgtacc tttgatgatt tgcagactac aagcattcaa      10654
ggtgctgtgt tatatattac ttgcttggag aataatactt cttaaaaatt gaaattcaga      10714
aattttaaat cagacaaagc ttttgtgcat ggcccactta aatggctatt ttgaaataat      10774
gatagtggat atagaaggat tattctgtaa taggatgaga ctgttccttt tgtcatggag      10834
atcataatca tattttttgta aattttttatt attttttttgg ttttgtgtcc atcctgcaca     10894
ctattactgg gtaggtacat ggttttttaa catggtttat ctttcaaaac tataaaggca      10954
ttgcaaacag aagacaggtc atttattttt cttccaaaag catctaaaat gagattttga      11014
tatttgaggt cataaagagg tgagagaaca gacaacagtt gggaaagcta tttctcttga      11074
aattgtttgg ccttaattac tacagtgtcc tagtaccacc catacgtttc caagaagta      11134 gatccctgta aatgcctttg tctctggact tttgagtaaa atagtagggt gtgctttgca      11194
aaatgtcatc gttgatgttg agtttcagag tcttttaatta ggaagctgaa atctgtatat     11254
cgagatttgt aaatcatcta aattgcagag taatgtttta gaatactgct taagggattg     11314
gcattaaagc cttttttaaa aaagaaatgc aataatttcc tcaaatcctc actcattaga     11374
cctctactaa ctatagtgct gactttttttt ttttttttacc ctaaagtctg gaattccaaa    11434
gaaatgcttc accatttccc ccattattat agccacctgg aagcagtatt catgtattag     11494
atcaaaaaca caacaaagaa ttatgaaagg ttgtttcctg gtatgcaatg catgatgaca     11554
tgaacttaca gaacagagag aagggaggct ccatgtttat ttaaagagga aattttttatt    11614 ttctggttac ctacttttac atgggttaca tcaaatccca cgatgaggtt taaaaattct     11674
catagataat caaacgtcat tacttggctt actgaaattc agactttttct tttttcttcc    11734 ctgtttttct ctatcaaatt ag aa tct ttg gaa gaa cta cca gaa acg agt      11785
                        Glu Ser Leu Glu Glu Leu Pro Glu Thr Ser
                                     120              125 ggg aaa aca acc cgg aga ttc ttc ttt aat tta agt tct atc ccc acg        11833
Gly Lys Thr Thr Arg Arg Phe Phe Phe Asn Leu Ser Ser Ile Pro Thr
           130                 135                 140 gag gag ttt atc acc tca gca gag ctt cag gtt ttc cga gaa cag atg        11881
Glu Glu Phe Ile Thr Ser Ala Glu Leu Gln Val Phe Arg Glu Gln Met
       145                 150                 155 caa gat gct tta gga aac aat agc agt ttc cat cac cga att aat att        11929
Gln Asp Ala Leu Gly Asn Asn Ser Ser Phe His His Arg Ile Asn Ile
       160                 165                 170 tat gaa atc ata aaa cct gca aca gcc aac tcg aaa ttc ccc gtg acc        11977
Tyr Glu Ile Ile Lys Pro Ala Thr Ala Asn Ser Lys Phe Pro Val Thr
175                 180                 185 aga ctt ttg gac acc agg ttg gtg aat cag aat gca agc agg tgg gaa        12025
Arg Leu Leu Asp Thr Arg Leu Val Asn Gln Asn Ala Ser Arg Trp Glu
190                 195                 200                 205 agt ttt gat gtc acc ccc gct gtg atg cgg tgg act gca cag gga cac        12073
Ser Phe Asp Val Thr Pro Ala Val Met Arg Trp Thr Ala Gln Gly His
           210                 215                 220 gcc aac cat gga ttc gtg gtg gaa gtg gcc cac ttg gag gag aaa caa        12121
Ala Asn His Gly Phe Val Val Glu Val Ala His Leu Glu Glu Lys Gln
           225                 230                 235 ggt gtc tcc aag aga cat gtt agg ata agc agg tct ttg cac caa gat        12169
Gly Val Ser Lys Arg His Val Arg Ile Ser Arg Ser Leu His Gln Asp
           240                 245                 250
```

```
gaa cac agc tgg tca cag ata agg cca ttg cta gta act ttt ggc cat    12217
Glu His Ser Trp Ser Gln Ile Arg Pro Leu Leu Val Thr Phe Gly His
    255                 260                 265 gat gga aaa ggg cat cct ctc cac aaa aga gaa aaa cgt caa gcc aaa    12265
Asp Gly Lys Gly His Pro Leu His Lys Arg Glu Lys Arg Gln Ala Lys
270                 275                 280                 285 cac aaa cag cgg aaa cgc ctt aag tcc agc tgt aag aga cac cct ttg    12313
His Lys Gln Arg Lys Arg Leu Lys Ser Ser Cys Lys Arg His Pro Leu
                290                 295                 300 tac gtg gac ttc agt gac gtg ggg tgg aat gac tgg att gtg gct ccc    12361
Tyr Val Asp Phe Ser Asp Val Gly Trp Asn Asp Trp Ile Val Ala Pro
                    305                 310                 315 ccg ggg tat cac gcc ttt tac tgc cac gga gaa tgc cct ttt cct ctg    12409
Pro Gly Tyr His Ala Phe Tyr Cys His Gly Glu Cys Pro Phe Pro Leu
                320                 325                 330 gct gat cat ctg aac tcc act aat cat gcc att gtt cag acg ttg gtc    12457
Ala Asp His Leu Asn Ser Thr Asn His Ala Ile Val Gln Thr Leu Val
                335                 340                 345 aac tct gtt aac tct aag att cct aag gca tgc tgt gtc ccg aca gaa    12505
Asn Ser Val Asn Ser Lys Ile Pro Lys Ala Cys Cys Val Pro Thr Glu
350                 355                 360                 365 ctc agt gct atc tcg atg ctg tac ctt gac gag aat gaa aag gtt gta    12553
Leu Ser Ala Ile Ser Met Leu Tyr Leu Asp Glu Asn Glu Lys Val Val
                    370                 375                 380 tta aag aac tat cag gac atg gtt gtg gag ggt tgt ggg tgt cgc tag    12601
Leu Lys Asn Tyr Gln Asp Met Val Val Glu Gly Cys Gly Cys Arg *
                385                 390                 395 tacagcaaaa ttaaatacat aaatatatat atatatatat attttagaaa aagaaaaaa   12661 acaaacaaac aaaaaaaccc caccccagtt gacactttaa tatttcccaa tgaagacttt   12721
atttatggaa tggaatggaa aaaaaaacag ctattttgaa aatatattta tatctacgaa   12781
aagaagttgg gaaaacaaat attttaatca gagaattatt ccttaaagat ttaaaatgta   12841
tttagttgta cattttatat gggttcaacc ccagcacatg aagtataatg gtcagattta   12901
ttttgtattt atttactatt ataaccactt tttaggaaaa aaatagctaa tttgtattta   12961
tatgtaatca aagaagtat cgggtttgta cataattttc caaaaattgt agttgttttc    13021
agttgtgtgt atttaagatg aaaagtctac atggaaggtt actctggcaa agtgcttagc   13081
acgtttgctt ttttgcagtg ctactgttga gttcacaagt tcaagtccag aaaaaaaaag   13141
tggataatcc actctgctga ctttcaagat tattatatta ttcaattctc aggaatgttg   13201
cagagtgatt gtccaatcca tgagaattta catccttatt aggtggaata tttggataag   13261
aaccagacat tgctgatcta ttatagaaac tctcctcctg cccttaatt tacagaaaga    13321 ataaagcagg atccatagaa ataattagga aaacgatgaa cctgcaggaa agtgaatgat   13381
ggtttgttgt tcttctttcc taaattagtg atcccttcaa aggggctgat ctggccaaag   13441
tattcaataa aacgtaagat ttcttcatta ttgatattgt ggtcatatat atttaaaatt   13501
gatatctcgt ggccctcatc aagggttgga aatttatttg tgttttacct ttacctcatc   13561
tgagagctct ttattctcca aagaacccag ttttctaact ttttgcccaa cacgcagcaa   13621
aattatgcac atcgtgtttt ctgcccaccc tctgttctct gacctatcag cttgcttttc   13681
tttccaaggt tgtgtgtttg aacacatttc tccaaatgtt aaacctattt cagataataa   13741
atatcaaatc tctggcattt cattctataa agtccaacct gtaagagaaa atggtgcatt   13801
tgtatagcgc ttcaatgat gaccttgtgt ttgcattttt gtttctgaag ttatatatttt    13861 tagaggggt gggggaaagg taatgaatgg ctggaaaatt gcaggcaagt tatttgataa    13921
```

-continued

```
gtcatatttg cactaaaggt gttaccagtg atttagtatt tttcaaatga acttctttgg  13981
ggcagaaaga tttaagggaa aactaaagcc tacaaaacaa gcaaaacctg gataacccga  14041
gataaagttt cagagataat agcccatgca acagaggcaa cggtgccaga aaattagaaa  14101
gggaaagtgt cggagatcag cttctataag aacatctgcc agttggactg acgcccaaac  14161
agaatgaagt caaattaggc tgctcagatt gaacacttac cagagtgtca gggcttctgt  14221
accctgggtt agaatcagac caaggaaggg ttcagcagat gttcataaga gcagggcacc  14281
cacaactacc cactatttta ctggcagtat tttaggtcag tttccaggac tttgcatccc  14341
ctctgatcct gccatgcatg attggtgaaa cctacctcta atctccttgg aattggctaa  14401
aaaacagtgt gtttataatg aacagactgt ttataatcaa attcttccta ggaattaact  14461
tttgatgact atgagcttag ttacagttcg gaggttatga ggttatgtaa accttatctt  14521
taaatgtgca tgacagttat cttttactaa tgctggttaa cttttaaaat cttgcagctc  14581 cttttatct ctagttctat tgttcttgat taggtgagaa ccattagatc atacccaact  14641
gaggggattg gggtcttgtt tgttctccag ctgttcttca ccctctattg ccatggacat  14701
gaaggacaga ctgcacggtc ttaacatgtt aaaacgaatg acccatgttt tctcatat    14759
```

<210> SEQ ID NO 2
<211> LENGTH: 396
<212> TYPE: PRT
<213> ORGANISM: Homo sapien

<400> SEQUENCE: 2

```
Met Val Ala Gly Thr Arg Cys Leu Leu Ala Leu Leu Leu Pro Gln Val
  1               5                  10                  15

Leu Leu Gly Gly Ala Ala Gly Leu Val Pro Glu Leu Gly Arg Arg Lys
                 20                  25                  30

Phe Ala Ala Ala Ser Ser Gly Arg Pro Ser Ser Gln Pro Ser Asp Glu
             35                  40                  45

Val Leu Ser Glu Phe Glu Leu Arg Leu Leu Ser Met Phe Gly Leu Lys
         50                  55                  60

Gln Arg Pro Thr Pro Ser Arg Asp Ala Val Val Pro Pro Tyr Met Leu
 65                  70                  75                  80

Asp Leu Tyr Arg Arg His Ser Gly Gln Pro Gly Ser Pro Ala Pro Asp
                 85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220
```

-continued

```
Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
            245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
            275                 280                 285

Arg Lys Arg Leu Lys Ser Ser Cys Lys Arg His Pro Leu Tyr Val Asp
            290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
            355                 360                 365

Ile Ser Met Leu Tyr Leu Asp Glu Asn Glu Lys Val Val Leu Lys Asn
    370                 375                 380

Tyr Gln Asp Met Val Val Glu Gly Cys Gly Cys Arg
385                 390                 395
```

HUMAN OSTEOPOROSIS GENE

BACKGROUND OF THE INVENTION

Osteoporosis is a debilitating disease characterized by low bone mass and deterioration of bone tissue, as defined by decreased bone mineral density (BMD). A direct result of the experienced microarchitectural deterioration is susceptibility to fractures and skeletal fragility, ultimately causing high mortality, morbidity and medical expenses worldwide. Postmenopausal woman are at greater risk than others because the estrogen deficiency and corresponding decrease in bone mass experienced during menopause increase both the probability of osteoporotic fracture and the number of potential fracture sites. Yet aging women are not the only demographic group at risk. Young woman who are malnourished, ammenorrheic, or insufficiently active are at risk of inhibiting bone mass development at an early age. Furthermore, androgens play a role in the gain of bone mass during puberty, so elderly or hypogonadal men face the risk of osteoporosis if their bones were insufficiently developed.

The need to find a cure for this disease is complicated by the fact that there are many contributing factors that cause osteoporosis. Nutrition (particularly calcium, vitamin D and vitamin K intake), hormone levels, age, sex, race, body weight, activity level, and genetic factors all account for the variance seen in bone mineral density among individuals. Currently, the drugs approved to treat osteoporosis act as inhibitors of bone reabsorption, and include methods such as hormone replacement therapy (HRT), selective estrogen receptor modulators, calcitonin, and biophosphonates. However, these treatments may not individually reduce risk with consistent results and while some therapies improve BMD when coadministered, others show no improvement or even lose there efficacy when used in combination. Clearly, as life expectancy increases and health and economic concerns of osteoporosis grow, a solution for the risks associated with this late-onset disease is in great demand. Early diagnosis of the disease or predisposition to the disease would be desirable.

SUMMARY OF THE INVENTION

As described herein, it has been discovered that polymorphisms in the gene for human bone morphogenetic protein 2 (BMP2) have been correlated through human linkage studies to a number of osteoporosis phenotypes. In particular, it has been discovered that one or more single nucleotide polymorphisms within the nucleotide sequence encoding the BMP2 gene product is correlated to osteoporosis. Accordingly, this invention pertains to an isolated nucleic acid molecule containing the BMP2 gene of SEQ ID NO:1 (Table 1) having at least one altered nucleotide and to gene products encoded thereby (referred to herein as a "variant BMP2 gene" or "variant BMP2 gene product").

A number of polymorphisms have been observed in the BMP2 gene, as follows:
Promoter Region:
  A to G at nucleotide position 420;
  A to G at nucleotide position 472;
  G to C at nucleotide position 1464;
  G to A at nucleotide position 1722;
  C to A at nucleotide position 1914;
Coding Region:
  T to G at nucleotide position 3747; resulting in an amino acid change from serine to alanine at amino acid position 37;
  A to G at nucleotide position 3899; no amino acid change;
  G to T at nucleotide position 3918; resulting in an amino acid change from alanine to serine at amino acid position 94;
  A to T at nucleotide position 11980; resulting in an amino acid change from arginine to serine at amino acid position 189;
3' UTR and Downstream Region:
  C to T at nucleotide position 12571;
  T to C at nucleotide position 13066;
  A to G at nucleotide position 13209;
  C to A at nucleotide position 13296; and
  at least one deletion in nucleotides at positions 13533–13536.

All numbering is relative to SEQ ID NO. 1. Thus, in preferred embodiments, the isolated nucleic acid molecule of the invention can have one or a combination of these single nucleotide polymorphisms. These polymorphisms may be part of a group of other polymorphisms in the BMP2 gene which contributes to the presence, absence or severity of osteoporosis.

The invention also relates to DNA constructs comprising the nucleic acid molecules described herein operatively linked to a regulatory sequence, and to recombinant host cells, such as bacterial cells, fungal cells, plant cells, insect cells and mammalian cells, comprising the nucleic acid molecules described herein operatively linked to a regulatory sequence.

The invention also pertains to methods of diagnosing osteoporosis in an individual. The methods include detecting the presence of a mutation in the BMP2 gene. The invention additionally pertains to pharmaceutical compositions comprising the BMP2 nucleic acids of the invention and to kits for carrying out the methods described herein. The methods of the invention allow the accurate diagnosis of osteoporosis at or before disease onset, thus reducing or minimizing the debilitating effects of osteoporosis.

DETAILED DESCRIPTION OF THE INVENTION

As described herein, Applicants have completed a genome wide scan on patients with various forms of osteoporosis and identified a region on chromosome 20 linked to osteoporosis. Until now there have been no known linkage studies of osteoporosis in humans showing any connection to this region of the chromosome. Based on the linkage studies conducted, Applicants have discovered a direct relationship between BMP2 and osteoporosis. Although the BMP2 gene from normal individuals is known, there have been no studies directly investigating BMP2 and osteoporosis. Moreover, there have been no variant forms reported that have been associated with osteoporosis. The linkage studies are based on four genome wide scans encompassing affected persons having different osteoporosis phenotypes; i.e., hip, spine, combined and combined severe (e.g., patients having vertebral compression fracture, hip fracture, other osteoporosis related low impact fracture). From the data obtained in the linkage study, a region on chromosome 20, specifically the BMP2 gene, was identified. The variant BMP2 gene has previously unreported nucleotide changes that were observed in the patient population, as follows:
Promoter Region:
  A to G at nucleotide position 420;
  A to G at nucleotide position 472;

G to C at nucleotide position 1464;
G to A at nucleotide position 1722;
C to G at nucleotide position 1914;
Coding Region:
   T to G at nucleotide position 3747; resulting in an amino acid change from serine to alanine at amino acid position 37;
   A to G at nucleotide position 3899; no amino acid change;
   G to T at nucleotide position 3918; resulting in an amino acid change from alanine to serine at amino acid position 94;
   A to T at nucleotide position 11980; resulting in an amino acid change from arginine to serine at amino acid position 189;
3' UTR and Downstream Region:
   C to T at nucleotide position 12571;
   T to C at nucleotide position 13066;
   A to G at nucleotide position 13209;
   C to A at nucleotide position 13296; and
at least one deletion in nucleotides at positions 13533–13536.
All nucleotide positions are relative to SEQ ID NO: 1. The polymorphism at nucleotide position 3747 appears statistically more frequent in the osteoporosis test population than in the control population.

NUCLEIC ACIDS OF THE INVENTION

Accordingly, the invention pertains to an isolated nucleic acid molecule comprising the human BMP2 gene having at least one nucleotide alteration and correlated with incidence of osteoporosis. The term, "variant BMP2", as used herein, refers to an isolated nucleic acid molecule in chromosome 20 having at least one altered nucleotide that is associated with a susceptibility to a number of osteoporosis phenotypes, and also to a portion or fragment of the isolated nucleic acid molecule containing the alteration (e.g., cDNA or the gene) and encoding a variant BMP2 polypeptide (e.g., the polypeptide having SEQ ID NO: 2, as shown in Table 1). In a preferred embodiment, the isolated nucleic acid molecules comprises a polymorphism selected from the group consisting of: A to G at nucleotide position 420; A to G at nucleotide position 472; G to C at nucleotide position 1464; G to A at nucleotide position 1722; C to G at nucleotide position 1914; T to G at nucleotide position 3747, resulting in an amino acid change from serine to alanine at amino acid position 37; A to G at nucleotide position 3899, no amino acid change; G to T at nucleotide position 3918, resulting in an amino acid change from alanine to serine at amino acid position 94; A to T at nucleotide position 11980, resulting in an amino acid change from arginine to serine at amino acid position 189; C to T at nucleotide position 12571; T to C at nucleotide position 13066; A to G at nucleotide position 13209; C to A at nucleotide position 13296; at least one deletion in nucleotides at positions 13533–13536 and combinations thereof, of the BMP2 gene.

The isolated nucleic acid molecules of the present invention can be RNA, for example, mRNA, or DNA, such as cDNA and genomic DNA. DNA molecules can be double-stranded or single-stranded; single stranded RNA or DNA can be either the coding, or sense, strand or the non-coding, or antisense, strand. The nucleic acid molecule can include all or a portion of the coding sequence of the gene and can further comprise additional non-coding sequences such as introns and non-coding 3' and 5' sequences (including regulatory sequences, for example). Additionally, the nucleic acid molecule can be fused to a marker sequence, for example, a sequence that encodes a polypeptide to assist in isolation or purification of the polypeptide. Such sequences include, but are not limited to, those which encode a glutathione-S-transferase (GST) fusion protein and those which encode a hemaglutin A (HA) polypeptide marker from *influenza*.

An "isolated" nucleic acid molecule, as used herein, is one that is separated from nucleic acids which normally flank the gene or nucleotide sequence (as in genomic sequences) and/or has been completely or partially purified from other transcribed sequences (e.g., as in an RNA library). For example, an isolated nucleic acid of the invention may be substantially isolated with respect to the complex cellular milieu in which it naturally occurs, or culture medium when produced by recombinant techniques, or chemical precursors or other chemicals when chemically synthesized. In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid molecule comprises at least about 50, 80 or 90% (on a molar basis) of all macromolecular species present. With regard to genomic DNA, the term "isolated" also can refer to nucleic acid molecules which are separated from the chromosome with which the genomic DNA is naturally associated. For example, the isolated nucleic acid molecule can contain less than about 5 kb, 4 kb, 3 kb, 2 kb, 1 kb, 0.5 kb or 0.1 kb of nucleotides which flank the nucleic acid molecule in the genomic DNA of the cell from which the nucleic acid molecule is derived.

The nucleic acid molecule can be fused to other coding or regulatory sequences and still be considered isolated. Thus, recombinant DNA contained in a vector is included in the definition of "isolated" as used herein. Also, isolated nucleic acid molecules include recombinant DNA molecules in heterologous host cells, as well as partially or substantially purified DNA molecules in solution. "Isolated" nucleic acid molecules also encompass in vivo and in vitro RNA transcripts of the DNA molecules of the present invention. An isolated nucleic acid molecule or nucleotide sequence can include a nucleic acid molecule or nucleotide sequence which is synthesized chemically or by recombinant means. Therefore, recombinant DNA contained in a vector are included in the definition of "isolated" as used herein. Also, isolated nucleotide sequences include recombinant DNA molecules in heterologous organisms, as well as partially or substantially purified DNA molecules in solution. In vivo and in vitro RNA transcripts of the DNA molecules of the present invention are also encompassed by "isolated" nucleotide sequences. Such isolated nucleotide sequences are useful in the manufacture of the encoded polypeptide, as probes for isolating homologous sequences (e.g., from other mammalian species), for gene mapping (e.g., by in situ hybridization with chromosomes), or for detecting expression of the gene in tissue (e.g., human tissue), such as by Northern blot analysis The present invention also pertains to nucleic acid molecules which are not necessarily found in nature but which encode a BMP2 polypeptide (e.g., a polypeptide having the amino acid sequence of SEQ ID NO: 2). Thus, for example, DNA molecules which comprise a sequence that is different from the naturally-occurring nucleotide sequence but which, due to the degeneracy of the genetic code, encode an BMP2 polypeptide of the present invention are also the subject of this invention. The invention also encompasses variants of the nucleotide sequences of the intention, such as those encoding portions, analogues or derivatives of the BMP2 polypeptide. Such variants can be naturally-occurring, such as in the case of allelic variation, or non-naturally-occurring, such as those induced by various mutagens and mutagenic processes. Intended variations include, but are not limited to, addition, deletion and substitution of one or more nucleotides which can result in conservative or non-conservative amino acid changes, including additions and deletions. Preferably the nucleotide (and/or resultant amino acid) changes are silent or conserved; that is, they do not alter the characteristics or activity of the BMP2 polypeptide.

Other alterations of the nucleic acid molecules of the invention can include, for example, labeling, methylation, intemucleotide modifications such as uncharged linkages (e.g., methyl phosphonates, phosphotriesters, phosphoamidates, carbamates), charged linkages (e.g., phosphorothioates, phosphorodithioates), pendent moieties (e.g., polypeptides), intercalators (e.g., acridine, psoralen), chelators, alkylators, and modified linkages (e.g., alpha anomeric nucleic acids). Also included are synthetic molecules that mimic nucleic acid molecules in the ability to bind to a designated sequences via hydrogen bonding and other chemical interactions. Such molecules include, for example, those in which peptide linkages substitute for phosphate linkages in the backbone of the molecule.

The invention also pertains to nucleic acid molecules which hybridize under high stringency hybridization conditions, such as for selective hybridization, to a nucleotide sequence described herein (e.g., nucleic acid molecules which specifically hybridize to a nucleotide sequence encoding polypeptides described herein, and, optionally, have an activity of the polypeptide). In one embodiment, the invention includes variants described herein which hybridize under high stringency hybridization conditions (e.g., for selective hybridization) to a nucleotide sequence comprising a nucleotide sequence selected from SEQ ID NO: 1 or the complement of SEQ ID NO: 1.

Such nucleic acid molecules can be detected and/or isolated by specific hybridization (e.g., under high stringency conditions). "Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity which is less than perfect (e.g., 70%, 75%, 85%, 95%). For example, certain high stringency conditions can be used which distinguish perfectly complementary nucleic acids from those of less complementarity. "High stringency conditions", "moderate stringency conditions" and "low stringency conditions" for nucleic acid hybridizations are explained on pages 2.10.1–2.10.16 and pages 6.3.1–6.3.6 in *Current Protocols in Molecular Biology* (Ausubel, F. M. et al., "*Current Protocols in Molecular Biology*", John Wiley & Sons, (1998), the entire teachings of which are incorporated by reference herein). The exact conditions which determine the stringency of hybridization depend not only on ionic strength (e.g., 0.2×SSC, 0.1×SSC), temperature (e.g., room temperature, 42° C., 68° C.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, equivalent conditions can be determined by varying one or more of these parameters while maintaining a similar degree of identity or similarity between the two nucleic acid molecules. Typically, conditions are used such that sequences at least about 60%, at least about 70%, at least about 80%, at least about 90% or at least about 95% or more identical to each other remain hybridized to one another. By varying hybridization conditions from a level of stringency at which no hybridization occurs to a level at which hybridization is first observed, conditions which will allow a given sequence to hybridize (e.g., selectively) with the most similar sequences in the sample can be determined.

Exemplary conditions are described in Krause, M. H. and S. A. Aaronson, *Methods in Enzymology*, 200:546–556 (1991). Also, in, Ausubel, et al., "*Current Protocols in Molecular Biology*", John Wiley & Sons, (1998), which describes the determination of washing conditions for moderate or low stringency conditions. Washing is the step in which conditions are usually set so as to determine a minimum level of complementarity of the hybrids. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in $T_m$ of ~17° C. Using these guidelines, the washing temperature can be determined empirically for high, moderate or low stringency, depending on the level of mismatch sought.

For example, a low stringency wash can comprise washing in a solution containing 0.2×SSC/0.1% SDS for 10 min at room temperature; a moderate stringency wash can comprise washing in a prewarmed solution (42° C.) solution containing 0.2×SSC/0.1% SDS for 15 min at 42° C.; and a high stringency wash can comprise washing in prewarmed (68° C.) solution containing 0.1×SSC/0.1% SDS for 15 min at 68° C. Furthermore, washes can be performed repeatedly or sequentially to obtain a desired result as known in the art. Equivalent conditions can be determined by varying one or more of the parameters given as an example, as known in the art, while maintaining a similar degree of identity or similarity between the target nucleic acid molecule and the primer or probe used.

The percent identity of two nucleotide or amino acid sequences can be determined by aligning the sequences for optimal comparison purposes (e.g., gaps can be introduced in the sequence of a first sequence). The nucleotides or amino acids at corresponding positions are then compared, and the percent identity between the two sequences is a function of the number of identical positions shared by the sequences (i.e., % identity=# of identical positions/total # of positions×100). In certain embodiments, the length of a sequence aligned for comparison purposes is at least 30%, preferably at least 40%, more preferably at least 60%, and even more preferably at least 70%, 80% or 90% of the length of the reference sequence. The actual comparison of the two sequences can be accomplished by well-known methods, for example, using a mathematical algorithm. A preferred, non-limiting example of such a mathematical algorithm is described in Karlin et al., *Proc. Natl. Acad. Sci. USA*, 90:5873–5877 (1993). Such an algorithm is incorporated into the NBLAST and XBLAST programs (version 2.0) as described in Altschul et al., *Nucleic Acids Res.*, 25:389–3402 (1997). When utilizing BLAST and Gapped BLAST programs, the default parameters of the respective programs (e.g., NBLAST) can be used. In one embodiment, parameters for sequence comparison can be set at score=100, wordlength=12, or can be varied (e.g., W=5 or W=20).

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package (Accelrys, Cambridge, UK). When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (1994) *Comput. Appl. Biosci.*, 10:3–5; and FASTA described in Pearson and Lipman (1988) *PNAS*, 85:2444–8.

In another embodiment, the percent identity between two amino acid sequences can be accomplished-using the GAP program in the CGC software package using either a Blossom 63 matrix or a PAM250 matrix, and a gap weight of 12, 10, 8, 6, or 4 and a length weight of 2, 3, or 4. In yet another embodiment, the percent identity between two nucleic acid sequences can be accomplished using the GAP program in the CGC software package, using a gap weight of 50 and a length weight of 3.

The present invention also provides isolated nucleic acid molecules that contain a fragment or portion that hybridizes under highly stringent conditions to a nucleotide sequence comprising a nucleotide sequence selected from SEQ ID NO: 1 and the complement of SEQ ID NO: 1. The nucleic acid fragments of the invention are at least about 15, preferably at least about 18, 20, 23 or 25 nucleotides, and can be 30, 40, 50, 100, 200 or more nucleotides in length. Longer fragments, for example, 30 or more nucleotides in length, which encode antigenic polypeptides described herein are particularly useful, such as for the generation of antibodies as described below.

In a related aspect, the nucleic acid fragments of the invention are used as probes or primers in assays such as those described herein. "Probes" are oligonucleotides that hybridize in a base-specific manner to a complementary strand of nucleic acid molecules. Such probes include polypeptide nucleic acids, as described in Nielsen et al., *Science*, 254, 1497–1500 (1991). Typically, a probe comprises a region of nucleotide sequence that hybridizes under highly stringent conditions to at least about 15, typically about 20–25, and more typically about 40, 50 or 75, consecutive nucleotides of a nucleic acid molecule comprising a nucleotide sequence selected from SEQ ID NO: 1 and the complement of SEQ ID NO: 1. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides.

The nucleic acid molecules of the invention such as those described above can be identified and isolated using standard molecular biology techniques and the sequence information provided in SEQ ID NO: 1. For example, nucleic acid molecules can be amplified and isolated by the polymerase chain reaction using synthetic oligonucleotide primers designed based on one or more of the sequences provided in SEQ ID NO: 1 and/or the complement of SEQ ID NO: 1. See generally *PCR Technology: Principles and Applications for DNA Amplification* (ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.*, 19:4967 (1991); Eckert et al., *PCR Methods and Applications*, 1:17 (1991); PCR (eds. McPherson et al., IRL Press, Oxford); and U.S. Pat. No. 4,683,202. The nucleic acid molecules can be amplified using cDNA, mRNA or genomic DNA as a template, cloned into an appropriate vector and characterized by DNA sequence analysis.

Other suitable amplification methods include the ligase chain reaction (LCR) (see Wu and Wallace, *Genomics*, 4:560 (1989), Landegren et al., *Science*, 241:1077 (1988), transcription amplification (Kwoh et al., *Proc. Natl. Acad. Sci. USA*, 86:1173 (1989)), and self-sustained sequence replication (Guatelli et al., *Proc. Nat. Acad. Sci. USA*, 87:1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The amplified DNA can be radiolabelled and used as a probe for screening a cDNA library derived from human cells, mRNA in zap express, ZIPLOX or other suitable vector. Corresponding clones can be isolated, DNA can obtained following in vivo excision, and the cloned insert can be sequenced in either or both orientations by art recognized methods to identify the correct reading frame encoding a polypeptide of the appropriate molecular weight. For example, the direct analysis of the nucleotide sequence of nucleic acid molecules of the present invention can be accomplished using well-known methods that are commercially available. See, for example, Sambrook et al., *Molecular Cloning, A Laboratory Manual* (2nd Ed., CSHP, New York 1989); Zyskind et al., *Recombinant DNA Laboratory Manual*, (Acad. Press, 1988)). Using these or similar methods, the polypeptide and the DNA encoding the polypeptide can be isolated, sequenced and further characterized.

Antisense nucleic acid molecules of the invention can be designed using the nucleotide sequences of SEQ ID NO: 1 and/or the complement of SEQ ID NO: 1, and/or a portion of SEQ ID NO: 1 or the complement of SEQ ID NO: 1, and constructed using chemical synthesis and enzymatic ligation reactions using procedures known in the art. For example, an antisense nucleic acid molecule (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid molecule can be produced biologically using an expression vector into which a nucleic acid molecule has been subcloned in an antisense orientation (i.e., RNA transcribed from the inserted nucleic acid molecule will be of an antisense orientation to a target nucleic acid of interest).

In general, the isolated nucleic acid sequences of the invention can be used as molecular weight markers on Southern gels, and as chromosome markers which are labeled to map related gene positions. The nucleic acid sequences can also be used to compare with endogenous DNA sequences in patients to identify genetic disorders (e.g., a predisposition for or susceptibility to osteoporosis), and as probes, such as to hybridize and discover related DNA sequences or to subtract out known sequences from a sample. The nucleic acid sequences can further be used to derive primers for genetic fingerprinting, to raise anti-polypeptide antibodies using DNA immunization techniques, and as an antigen to raise anti-DNA antibodies or elicit immune responses. Portions or fragments of the nucleotide sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. Additionally, the nucleotide sequences of the invention can be used to identify and express recombinant polypeptides for analysis, characterization or therapeutic use, or as markers for tissues in which the corresponding polypeptide is expressed, either constitutively, during tissue differentiation, or in diseased states.

Another aspect of the invention pertains to nucleic acid constructs containing a nucleic acid moleucle selected from the group consisting of SEQ ID NO: 1 and the complement of SEQ ID NO: 1 (or a portion thereof). The constructs comprise a vector (e.g., an expression vector) into which a sequence of the invention has been inserted in a sense or antisense orientation. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids. However, the invention is intended to include such other forms of expression vectors, such as viral vectors (e.g., replication defective retroviruses, adenoviruses and adeno-associated viruses) that serve equivalent functions.

Preferred recombinant expression vectors of the invention comprise a nucleic acid molecule of the invention in a form suitable for expression of the nucleic acid molecule in a host cell. This means that the recombinant expression vectors include one or more regulatory sequences, selected on the basis of the host cells to be used for expression, which is operably linked to the nucleic acid sequence to be expressed. Within a recombinant expression vector, "operably or operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed and the level of expression of polypeptide desired. The expression vectors of the invention can be introduced into host cells to thereby produce polypeptides, including fusion polypeptides, encoded by nucleic acid molecules as described herein.

The recombinant expression vectors of the invention can be designed for expression of a polypeptide of the invention in prokaryotic or eukaryotic cells, e.g., bacterial cells such as *E. coli*, insect cells (using baculovirus expression vectors), yeast cells or mammalian cells. Suitable host cells are discussed further in Goeddel, supra. Alternatively, the recombinant expression vector can be transcribed and translated in vitro, for example using T7 promoter regulatory sequences and T7 polymerase.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a nucleic acid molecule of the invention can be expressed in bacterial cells (e.g., *E. coli*), insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing a foreign nucleic acid molecule (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those that confer resistance to drugs, such as G418, hygromycin and methotrexate. Nucleic acid molecules encoding a selectable marker can be introduced into a host cell on the same vector as the nucleic acid molecule of the invention or can be introduced on a separate vector. Cells stably transfected with the introduced nucleic acid molecule can be identified by drug selection (e.g., cells that have incorporated the selectable marker gene will survive, while the other cells die).

A host cell of the invention, such as a prokaryotic or eukaryotic host cell in culture, can be used to produce (i.e., express) a polypeptide of the invention. Accordingly, the invention further provides methods for producing a polypeptide using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which a nucleic acid molecule of the invention has been introduced. Such host cells can then be used to create non-human transgenic animals in which exogenous nucleotide sequences have been introduced into the genome or homologous recombinant animals in which endogenous nucleotide sequences have been altered. Such animals are useful for studying the function and/or activity of the nucleotide sequence and polypeptide encoded by the sequence and for identifying and/or evaluating modulators of their activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens and amphibians. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo* (Cold Spring Harbor Laboratory Press, Cold Spring Harbor, N.Y., 1986). Methods for constructing homologous recombination vectors and homologous recombinant animals are described further in Bradley (1991) *Current Opinion in Bio/Technology*, 2:823–829 and in PCT Publication Nos. WO 90/11354, WO 91/01140, WO 92/0968, and WO 93/04169. Clones of the non-human transgenic animals described herein can also be produced according to the methods described in Wilmut et al. (1997) *Nature*, 385:810–813 and PCT Publication Nos. WO 97/07668 and WO 97/07669.

POLYPEPTIDES OF THE INVENTION

The present invention also pertains to isolated BMP2 polypeptides, e.g., proteins, and variants thereof, as well as polypeptides encoded by nucleotide sequences described herein (e.g., other splicing variants). The term "polypeptide" refers to a polymer of amino acids, and not to a specific length; thus, peptides, oligopeptides and proteins are included within the definition of a polypeptide. As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be "isolated" or "purified."

The polypeptides of the invention can be purified to homogeneity. It is understood, however, that preparations in which the polypeptide is not purified to homogeneity are useful. The critical feature is that the preparation allows for the desired function of the polypeptide, even in the presence of considerable amounts of other components. Thus, the invention encompasses various degrees of purity. In one embodiment, the language "substantially free of cellular material" includes preparations of the polypeptide having less than about 30% (by dry weight) other proteins (i.e., contaminating protein), less than about 20% other proteins, less than about 10% other proteins, or less than about 5% other proteins.

When a polypeptide is recombinantly produced, it can also be substantially free of culture medium, i.e., culture medium represents less than about 20%, less than about 10%, or less than about 5% of the volume of the polypeptide preparation. The language "substantially free of chemical precursors or other chemicals" includes preparations of the polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, a polypeptide comprises an amino acid sequence encoded by a nucleic acid molecule comprising a nucleotide sequence selected from the group consisting of SEQ ID NO: 1 and complements and portions thereof, e.g., SEQ ID NO: 2, or a portion of SEQ ID NO: 2. However, the invention also encompasses sequence variants. Variants include a substantially homologous polypeptide encoded by the same genetic locus in an organism, i.e., an allelic variant, as well as other splicing variants. Variants also encompass polypeptides derived from other genetic loci in an organism, but having substantial homology to a polypeptide encoded by a nucleic acid molecule comprising a nucleotide sequence selected from the group consisting of SEQ ID NO: 1 and complements and portions thereof. Variants also include polypeptides substantially homologous or identical to these polypeptides but derived from another organism, i.e., an ortholog. Variants also include polypeptides that are substantially homologous or identical to these polypeptides that are produced by chemical synthesis. Variants also include polypeptides that are substantially homologous or identical to these polypeptides that are produced by recombinant methods.

As used herein, two polypeptides (or a region of the polypeptides) are substantially homologous or identical when the amino acid sequences are at least about 45–55%, typically at least about 70–75%, more typically at least about 80–85%, and most typically greater than about 90% or more homologous or identical. A substantially homologous amino acid sequence, according to the present invention, will be encoded by a nucleic acid molecule hybridizing to SEQ ID NO: 1, or portion thereof, under stringent conditions as more particularly described above.

To determine the percent homology or identity of two amino acid sequences, or of two nucleic acid sequences, the sequences are aligned for optimal comparison purposes (e.g., gaps can be introduced in the sequence of one polypeptide or nucleic acid molecule for optimal alignment with the other polypeptide or nucleic acid molecule). The amino acid residues or nucleotides at corresponding amino acid positions or nucleotide positions are then compared. When a position in one sequence is occupied by the same amino acid residue or nucleotide as the corresponding position in the other sequence, then the molecules are homologous at that position. As used herein, amino acid or nucleic acid "homology" is equivalent to amino acid or nucleic acid "identity". The percent homology between the two sequences is a function of the number of identical positions shared by the sequences (i.e., percent homology equals the number of identical positions/total number of positions times 100).

The invention also encompasses polypeptides having a lower degree of identity but having sufficient similarity so as to perform one or more of the same functions performed by a polypeptide encoded by a nucleic acid molecule of the invention. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr. Guidance concerning which amino acid changes are likely to be phenotypically silent are found in Bowie et al., Science 247:1306–1310 (1990).

A variant polypeptide can differ in amino acid sequence by one or more substitutions, deletions, insertions, inversions, fusions, and truncations or a combination of any of these. Further, variant polypeptides can be fully functional or can lack function in one or more activities. Fully functional variants typically contain only conservative variation or variation in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., Science, 244:1081–1085 (1989)). The latter procedure introduces single alanine mutations at every residue in the molecule. The resulting mutant molecules are then tested for biological activity in vitro, or in vitro proliferative activity. Sites that are critical for polypeptide activity can also be determined by structural analysis such as crystallization, nuclear magnetic resonance or photoaffinity labeling (Smith et al., J. Mol. Biol., 224:899–904 (1992); de Vos et al. Science, 255:306–312 (1992)).

The invention also includes polypeptide fragments of the polypeptides of the invention. Fragments can be derived from a polypeptide encoded by a nucleic acid molecule comprising SEQ ID NO: 1 or a portion thereof and the complements thereof. However, the invention also encompasses fragments of the variants of the polypeptides described herein. As used herein, a fragment comprises at least 6 contiguous amino acids. Useful fragments include those that retain one or more of the biological activities of the polypeptide as well as fragments that can be used as an immunogen to generate polypeptide-specific antibodies.

Biologically active fragments (peptides which are, for example, 6, 9, 12, 15, 16, 20, 30, 35, 36, 37, 38, 39, 40, 50, 100 or more amino acids in length) can comprise a domain, segment, or motif that has been identified by analysis of the polypeptide sequence using well-known methods, e.g., signal peptides, extracellular domains, one or more transmembrane segments or loops, ligand binding regions, zinc finger domains, DNA binding domains, acylation sites, glycosylation sites, or phosphorylation sites.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the polypeptide fragment and an additional region fused to the carboxyl terminus of the fragment.

The invention thus provides chimeric or fusion polypeptides. These comprise a polypeptide of the invention operatively linked to a heterologous protein or polypeptide having an amino acid sequence not substantially homologous to the polypeptide. "Operatively linked" indicates that the polypeptide and the heterologous protein are fused in-frame. The heterologous protein can be fused to the N-terminus or C-terminus of the polypeptide. In one embodiment the fusion polypeptide does not affect function of the polypeptide per se. For example, the fusion polypeptide can be a GST-fusion polypeptide in which the polypeptide sequences are fused to the C-terminus of the GST sequences. Other types of fusion polypeptides include, but are not limited to, enzymatic fusion polypeptides, for example β-galactosidase fusions, yeast two-hybrid GAL fusions, poly-His fusions and Ig fusions. Such fusion polypeptides, particularly poly-His fusions, can facilitate the purification of recombinant polypeptide. In certain host cells (e.g., mammalian host cells), expression and/or secretion of a polypeptide can be increased by using a heterologous signal sequence. Therefore, in another embodiment, the fusion polypeptide contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists. Bennett et al., Journal of Molecular Recognition, 8:52–58 (1995) and Johanson et al., The Journal of Biological Chemistry, 270,16:9459–9471 (1995). Thus, this invention also encompasses soluble fusion polypeptides containing a polypeptide of the invention and various portions of the constant regions of heavy or light chains of immunoglobulins of various subclass (IgG, IgM, IgA, IgE).

A chimeric or fusion polypeptide can be produced by standard recombinant DNA techniques. For example, DNA fragments coding for the different polypeptide sequences are ligated together in-frame in accordance with conventional techniques. In another embodiment, the fusion gene can be synthesized by conventional techniques including automated DNA synthesizers. Alternatively, PCR amplification of nucleic acid fragments can be carried out using anchor primers which give rise to complementary overhangs between two consecutive nucleic acid fragments which can subsequently be annealed and re-amplified to generate a chimeric nucleic acid sequence (see Ausubel et al., *Current Protocols in Molecular Biology*, 1992). Moreover, many expression vectors are commercially available that already encode a fusion moiety (e.g., a GST protein). A nucleic acid molecule encoding a polypeptide of the invention can be cloned into such an expression vector such that the fusion moiety is linked in-frame to the polypeptide.

The isolated polypeptide can be purified from cells that naturally express it, purified from cells that have been altered to express it (recombinant), or synthesized using known protein synthesis methods. In one embodiment, the polypeptide is produced by recombinant DNA techniques. For example, a nucleic acid molecule encoding the polypeptide is cloned into an expression vector, the expression vector introduced into a host cell and the polypeptide expressed in the host cell. The polypeptide can then be isolated from the cells by an appropriate purification scheme using standard protein purification techniques.

In general, polypeptides of the present invention can be used as a molecular weight marker on SDS-PAGE gels or on molecular sieve gel filtration columns using art-recognized methods. The polypeptides of the present invention can be used to raise antibodies or to elicit an immune response. The polypeptides can also be used as a reagent, e.g., a labeled reagent, in assays to quantitatively determine levels of the polypeptide or a molecule to which it binds (e.g., a receptor or a ligand) in biological fluids. The polypeptides can also be used as markers for cells or tissues in which the corresponding polypeptide is preferentially expressed, either constitutively, during tissue differentiation, or in a diseased state. The polypeptides can be used to isolate a corresponding binding partner, e.g., receptor or ligand, such as, for example, in an interaction trap assay, and to screen for peptide or small molecule antagonists or agonists of the binding interaction.

ANTIBODIES OF THE INVENTION

Polyclonal and/or monoclonal antibodies that specifically bind one form of the gene product but not to the other form of the gene product are also provided. Antibodies are also provided that bind a portion of either the variant or the reference gene product that contains the polymorphic site or sites. The invention provides antibodies to the polypeptides and polypeptide fragments of the invention, e.g., having an amino acid sequence encoded by SEQ ID NO: 2, or a portion thereof, or having an amino acid sequence encoded by a nucleic acid molecule comprising all or a portion of SEQ ID NO: 1. The term "antibody" as used herein refers to immunoglobulin molecules and immunologically active portions of immunoglobulin molecules, i.e., molecules that contain an antigen binding site that specifically binds an antigen. A molecule that specifically binds to a polypeptide of the invention is a molecule that binds to that polypeptide or a fragment thereof, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind to a polypeptide of the invention. The term "monoclonal antibody" or "monoclonal antibody composition", as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

Polyclonal antibodies can be prepared as described above by immunizing a suitable subject with a desired immunogen, e.g., polypeptide of the invention or fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature*, 256:495–497, the human B cell hybridoma technique (Kozbor et al. (1983) *Immunol. Today*, 4:72), the EBV-hybridoma technique (Cole et al. (1985), *Monoclonal Antibodies and Cancer Therapy*, Alan R. Liss, Inc., pp. 77–96) or trioma techniques. The technology for producing hybridomas is well known (see generally *Current Protocols in Immunology* (1994) Coligan et al. (eds.) John Wiley & Sons, Inc., New York, N.Y.). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to a polypeptide of the invention (see, e.g., *Current Protocols in Immunology*, supra; Galfre et al. (1977) *Nature*, 266:55052; R. H. Kenneth, in *Monoclonal Antibodies: A New Dimension In Biological Analyses*, Plenum Publishing Corp., New York, N.Y. (1980); and Lerner (1981) Yale *J. Biol. Med.*, 54:387–402. Moreover, the ordinarily skilled worker will appreciate that there are many variations of such methods that also would be useful.

Alternative to preparing monoclonal antibody-secreting hybridomas, a monoclonal antibody to a polypeptide of the invention can be identified and isolated by screening a recombinant combinatorial immunoglobulin library (e.g., an antibody phage display library) with the polypeptide to thereby isolate immunoglobulin library members that bind the polypeptide. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology*, 9:1370–1372; Hay et al. (1992)

*Hum. Antibod. Hybridomas*, 3:81–85; Huse et al. (1989) *Science*, 246:1275–1281; Griffiths et al. (1993) *EMBO J.*, 12:725–734.

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

In general, antibodies of the invention (e.g., a monoclonal antibody) can be used to isolate a polypeptide of the invention by standard techniques, such as affinity chromatography or inmunoprecipitation. A polypeptide-specific antibody can facilitate the purification of natural polypeptide from cells and of recombinantly produced polypeptide expressed in host cells. Moreover, an antibody specific for a polypeptide of the invention can be used to detect the polypeptide (e.g., in a cellular lysate, cell supernatant, or tissue sample) in order to evaluate the abundance and pattern of expression of the polypeptide. Antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H.

DIAGNOSTIC AND SCREENING ASSAYS OF THE INVENTION

The present invention also pertains to a method of diagnosing or aiding in the diagnosis of osteoporosis associated with the presence of the BMP2 gene or gene product in an individual. Diagnostic assays can be designed for determining BMP2 polypeptide and/or nucleic acid expression as well as activity of polypeptides of the invention, in the context of a biological sample (e.g., blood, serum, cells, tissue) to thereby determine whether an individual is afflicted with osteoporosis, or is at risk for (has a predisposition for or a susceptibility to) developing osteoporosis. The invention also provides for prognostic (or predictive) assays for determining whether an individual is susceptible to developing osteoporosis. For example, mutations in the gene can be assayed in a biological sample. Such assays can be used for prognostic or predictive purpose to thereby prophylactically treat an individual prior to the onset of symptoms associated with osteoporosis. Another aspect of the invention pertains to monitoring the influence of agents (e.g., drugs, compounds or other agents) on the expression or activity of polypeptides of the invention. These and other agents are described in further detail in the following sections.

DIAGNOSTIC ASSAYS

The nucleic acids, polypeptides and antibodies described herein can be used in methods of diagnosis of a suscepti-bility to osteoporosis, as well as in kits useful for diagnosis of a susceptibility to osteoporosis.

In one embodiment of the invention, diagnosis of a susceptibility to osteoporosis is made by detecting a polymorphism in BMP2 as described herein. The polymorphism can be a mutation in BMP2, such as the insertion or deletion of a single nucleotide, or of more than one nucleotide, resulting in a frame shift mutation; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of the gene; duplication of all or a part of the gene; transposition of all or a part of the gene; or rearrangement of all or a part of the gene. More than one such mutation may be present in a single gene. Such sequence changes cause a mutation in the polypeptide encoded by an BMP2 gene. For example, if the mutation is a frame shift mutation, the frame shift can result in a change in the encoded amino acids, and/or can result in the generation of a premature stop codon, causing generation of a truncated polypeptide. Alternatively, a polymorphism associated with a susceptibility to osteoporosis can be a synonymous mutation in one or more nucleotides (i.e., a mutation that does not result in a change in the polypeptide encoded by an BMP2 gene). Such a polymorphism may alter splicing sites, affect the stability or transport of mRNA, or otherwise affect the transcription or translation of the gene. An BMP2 gene that has any of the mutations described above is referred to herein as a "mutant gene."

In a first method of diagnosing a susceptibility to osteoporosis, hybridization methods, such as Southern analysis, Northern analysis, or in situ hybridizations, can be used (see Current Protocols in Molecular Biology, Ausubel, F. et al., eds., John Wiley & Sons, including all supplements through 1999). For example, a biological sample from a test subject (a "test sample") of genomic DNA, RNA, or cDNA, is obtained from an individual suspected of having, being susceptible to or predisposed for, or carrying a defect for, osteoporosis (the "test individual"). The individual can be an adult, child, or fetus. The test sample can be from any source which contains genomic DNA, such as a blood sample, sample of amniotic fluid, sample of cerebrospinal fluid, or tissue sample from skin, muscle, buccal or conjunctival mucosa, placenta, gastrointestinal tract or other organs. A test sample of DNA from fetal cells or tissue can be obtained by appropriate methods, such as by amniocentesis or chorionic villus sampling. The DNA, RNA, or cDNA sample is then examined to determine whether a polymorphism in bmp2 is present. The presence of the polymorphism can be indicated by hybridization of the gene in the genomic DNA, RNA, or cDNA to a nucleic acid probe. A "nucleic acid probe", as used herein, can be a DNA probe or an RNA probe; the nucleic acid probe contains at least one polymorphism in BMP2. The probe can be any of the nucleic acid molecules described above (e.g., the gene, a fragment, a vector comprising the gene, etc.).

To diagnose a susceptibility to osteoporosis, a hybridization sample is formed by contacting the test sample containing BMP2, with at least-one nucleic acid probe. A preferred probe for detecting mRNA or genomic DNA is a labeled nucleic acid probe capable of hybridizing to mRNA or genomic DNA sequences described herein. The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate mRNA or genomic DNA. For example, the nucleic acid probe can be all or a portion of SEQ ID NO: 1, or the complement of SEQ ID NO: 1, or a portion thereof. Other suitable probes for use in the diagnostic assays of the invention are described herein.

The hybridization sample is maintained under conditions which are sufficient to allow specific hybridization of the nucleic acid probe to BMP2. "Specific hybridization", as used herein, indicates exact hybridization (e.g., with no mismatches). Specific hybridization can be performed under high stringency conditions or moderate stringency conditions, for example, as described above. In a particularly preferred embodiment, the hybridization conditions for specific hybridization are high stringency.

Specific hybridization, if present, is then detected using standard methods. If specific hybridization occurs between the nucleic acid probe and BMP2 in the test sample, then BMP2 has the polymorphism that is present in the nucleic acid probe. More than one nucleic acid probe can also be used concurrently in this method. Specific hybridization of any one of the nucleic acid probes is indicative of a polymorphism in BMP2, and is therefore diagnostic for a susceptibility to osteoporosis.

In another hybridization method, Northern analysis (see Current Protocols in Molecular Biology, Ausubel, F. et al., eds., John Wiley & Sons, supra) is used to identify the presence of a polymorphism associated with a susceptibility to osteoporosis. For Northern analysis, a test sample of RNA is obtained from the individual by appropriate means. Specific hybridization of a nucleic acid probe, as described above, to RNA from the individual is indicative of a polymorphism in BMP2, and is therefore diagnostic for a susceptibility to osteoporosis.

For representative examples of use of nucleic acid probes, see, for example, U.S. Pat. Nos. 5,288,611 and 4,851,330.

Alternatively, a peptide nucleic acid (PNA) probe can be used instead of a nucleic acid probe in the hybridization methods described above. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, Nielsen, P. E. et al., *Bioconjugate Chemistry*, 1994, 5, American Chemical Society, p. 1 (1994). The PNA probe can be designed to specifically hybridize to a gene having a polymorphism associated with a susceptibility to osteoporosis. Hybridization of the PNA probe to BMP2 is diagnostic for a susceptibility to osteoporosis.

In another method of the invention, mutation analysis by restriction digestion can be used to detect a mutant gene, or genes containing a polymorphism(s), if the mutation or polymorphism in the gene results in the creation or elimination of a restriction site. A test sample containing genomic DNA is obtained from the individual. Polymerase chain reaction (PCR) can be used to amplify BMP2 (and, if necessary, the flanking sequences) in the test sample of genomic DNA from the test individual. RFLP analysis is conducted as described (see Current Protocols in Molecular Biology, supra). The digestion pattern of the relevant DNA fragment indicates the presence or absence of the mutation or polymorphism in BMP2, and therefore indicates the presence or absence of this susceptibility to osteoporosis.

Sequence analysis can also be used to detect specific polymorphisms in BMP2. A test sample of DNA or RNA is obtained from the test individual. PCR or other appropriate methods can be used to amplify the gene, and/or its flanking sequences, if desired. The sequence of BMP2, or a fragment of the gene, or cDNA, or fragment of the cDNA, or mRNA, or fragment of the mRNA, is determined, using standard methods. The sequence of the gene, gene fragment, cDNA, cDNA fragment, mRNA, or mRNA fragment is compared with the known nucleic acid sequence of the gene, cDNA (e.g., SEQ ID NO: 1) or mRNA, as appropriate. The presence of a polymorphism in BMP2 indicates that the individual has a susceptibility to osteoporosis.

Allele-specific oligonucleotides can also be used to detect the presence of a polymorphism in BMP2, through the use of dot-blot hybridization of amplified oligonucleotides with allele-specific oligonucleotide (ASO) probes (see, for example, Saiki, R. et al., (1986), *Nature (London)* 324:163–166). An "allele-specific oligonucleotide" (also referred to herein as an "allele-specific oligonucleotide probe") is an oligonucleotide of approximately 10–50 base pairs, preferably approximately 15–30 base pairs, that specifically hybridizes to BMP2, and that contains a polymorphism associated with a susceptibility to osteoporosis. An allele-specific oligonucleotide probe that is specific for particular polymorphisms in BMP2 can be prepared, using standard methods (see Current Protocols in Molecular Biology, supra). To identify polymorphisms in the gene that are associated with a susceptibility to osteoporosis, a test sample of DNA is obtained from the individual. PCR can be used to amplify all or a fragment of BMP2, and its flanking sequences. The DNA containing the amplified BMP2 (or fragment of the gene) is dot-blotted, using standard methods (see Current Protocols in Molecular Biology, supra), and the blot is contacted with the oligonucleotide probe. The presence of specific hybridization of the probe to the amplified BMP2 is then detected. Specific hybridization of an allele-specific oligonucleotide probe to DNA from the individual is indicative of a polymorphism in BMP2, and is therefore indicative of a susceptibility to osteoporosis.

In another embodiment, arrays of oligonucleotide probes that are complementary to target nucleic acid sequence segments from an individual, can be used to identify polymorphisms in BMP2. For example, in one embodiment, an oligonucleotide array can be used. Oligonucleotide arrays typically comprise a plurality of different oligonucleotide probes that are coupled to a surface of a substrate in different known locations. These oligonucleotide arrays, also described as "Genechips.™," have been generally described in the art, for example, U.S. Pat. No. 5,143,854 and PCT patent publication Nos. WO 90/15070 and 92/10092. These arrays can generally be produced using mechanical synthesis methods or light directed synthesis methods which incorporate a combination of photolithographic methods and solid phase oligonucleotide synthesis methods. See Fodor et al., *Science*, 251:767–777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186, the entire teachings of each of which are incorporated by reference herein. Techniques for the synthesis of these arrays using mechanical synthesis methods are described in, e.g., U.S. Pat. No. 5,384,261, the entire teachings of which are incorporated by reference herein.

Once an oligonucleotide array is prepared, a nucleic acid of interest is hybridized with the array and scanned for polymorphisms. Hybridization and scanning are generally carried out by methods described herein and also in, e.g., Published PCT Application Nos. WO 92/10092 and WO 95/11995, and U.S. Pat. No. 5,424,186, the entire teachings of which are incorporated by reference herein. In brief, a target nucleic acid sequence which includes one or more previously identified polymorphic markers is amplified by well known amplification techniques, e.g., PCR. Typically, this involves the use of primer sequences that are complementary to the two strands of the target sequence both upstream and downstream from the polymorphism. Asymmetric PCR techniques may also be used. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array.

Although primarily described in terms of a single detection block, e.g., for detection of a single polymorphism, arrays can include multiple detection blocks, and thus be capable of analyzing multiple, specific polymorphisms. In alternate arrangements, it will generally be understood that detection blocks may be grouped within a single array or in multiple, separate arrays so that varying, optimal conditions may be used during the hybridization of the target to the array. For example, it may often be desirable to provide for the detection of those polymorphisms that fall within G-C rich stretches of a genomic sequence, separately from those falling in A-T rich segments. This allows for the separate optimization of hybridization conditions for each situation.

Additional description of use of oligonucleotide arrays for detection of polymorphisms can be found, for example, in U.S. Pat. Nos. 5,858,659 and 5,837,832, the entire teachings of which are incorporated by reference herein.

Other methods of nucleic acid analysis can be used to detect polymorphisms in BMP2. Representative methods include direct manual sequencing (Church and Gilbert, (1988), *Proc. Natl. Acad. Sci. USA* 81:1991–1995; Sanger, F. et al. (1977) *Proc. Natl. Acad. Sci.* 74:5463–5467; Beavis et al. U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield, V. C. et al. (19891) *Proc. Natl. Acad. Sci. USA* 86:232–236), mobility shift analysis (Orita, M. et al. (1989) *Proc. Natl. Acad. Sci. USA* 86:2766–2770), restriction enzyme analysis (Flavell et al. (1978) *Cell* 15:25; Geever, et al. (1981) *Proc. Natl. Acad. Sci. USA* 78:5081); heteroduplex analysis; chemical mismatch cleavage (CMC) (Cotton et al. (1985) *Proc. Natl. Acad. Sci. USA* 85:4397–4401); RNase protection assays (Myers, R. M. et al. (1985) *Science* 230:1242); use of polypeptides which recognize nucleotide mismatches, such as *E. coli* mutS protein; allele-specific PCR, for example.

In another embodiment of the invention, diagnosis of a susceptibility to osteoporosis can also be made by examining expression and/or composition of an BMP2 polypeptide, by a variety of methods, including enzyme linked immunosorbent assays (ELISAs), Western blots, immunoprecipitations and immunofluorescence. A test sample from an individual is assessed for the presence of an alteration in the expression and/or an alteration in composition of the polypeptide encoded by BMP2. An alteration in expression of a polypeptide encoded by BMP2 can be, for example, an alteration in the quantitative polypeptide expression (i.e., the amount of polypeptide produced); an alteration in the composition of a polypeptide encoded by BMP2 is an alteration in the qualitative polypeptide expression (e.g., expression of a mutant BMP2 polypeptide or of a different splicing variant). Both such alterations (quantitative and qualitative) can also be present. An "alteration" in the polypeptide expression or composition, as used herein, refers to an alteration in expression or composition in a test sample, as compared with the expression or composition of polypeptide by BMP2 in a control sample. A control sample is a sample that corresponds to the test sample (e.g., is from the same type of cells), and is from an individual who is not affected by osteoporosis. An alteration in the expression or composition of the polypeptide in the test sample, as compared with the control sample, is indicative of a susceptibility to osteoporosis. Various means of examining expression or composition of the polypeptide encoded by BMP2 can be used, including spectroscopy, colorimetry, electrophoresis, isoelectric focusing, and immunoassays (e.g., David et al., U.S. Pat. No. 4,376,110) such as immunoblotting (see also Current Protocols in Molecular Biology, particularly chapter 10). For example, in one embodiment, an antibody capable of binding to the polypeptide (e.g., as described above), preferably an antibody with a detectable label, can be used. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Western blotting analysis, using an antibody as described above that specifically binds to a polypeptide encoded by a mutant BMP2, or an antibody that specifically binds to a polypeptide encoded by a non-mutant gene, can be used to identify the presence in a test sample of a polypeptide encoded by a polymorphic or mutant BMP2, or the absence in a test sample of a polypeptide encoded by a non-polymorphic or non-mutant gene. The presence of a polypeptide encoded by a polymorphic or mutant gene, or the absence of a polypeptide encoded by a non-polymorphic or non-mutant gene, is diagnostic for a susceptibility to osteoporosis.

In one embodiment of this method, the level or amount of polypeptide encoded by BMP2 in a test sample is compared with the level or amount of the polypeptide encoded by BMP2 in a control sample. A level or amount of the polypeptide in the test sample that is higher or lower than the level or amount of the polypeptide in the control sample, such that the difference is statistically significant, is indicative of an alteration in the expression of the polypeptide encoded by BMP2, and is diagnostic for a susceptibility to osteoporosis. Alternatively, the composition of the polypeptide encoded by BMP2 in a test sample is compared with the composition of the polypeptide encoded by BMP2 in a control sample. A difference in the composition of the polypeptide in the test sample, as compared with the composition of the polypeptide in the control sample, is diagnostic for a susceptibility to osteoporosis. In another embodiment, both the level or amount and the composition of the polypeptide can be assessed in the test sample and in the control sample. A difference in the amount or level of the polypeptide in the test sample, compared to the control sample; a difference in composition in the test sample, compared to the control sample; or both a difference in the amount or level, and a difference in the composition, is indicative of a susceptibility to osteoporosis.

Kits useful in the methods of diagnosis comprise components useful in any of the methods described herein, including for example, hybridization probes, restriction enzymes (e.g., for RFLP analysis), allele-specific oligonucleotides, antibodies which bind to mutant or to non-mutant (native) BMP2 polypeptide (e.g., to SEQ ID NO:2), means for amplification of nucleic acids comprising BMP2, or means for analyzing the nucleic acid sequence of BMP2 or for analyzing the amino acid sequence of an BMP2 polypeptide, etc.

SCREENING ASSAYS AND AGENTS IDENTIFIED THEREBY

The invention provides methods (also referred to herein as "screening assays") for identifying agents (e.g., antisense, polypeptides, peptidomimetics, small molecules or other drugs) which alter (e.g., increase or decrease) the activity of the polypeptides described herein. For example, such agents can be agents which bind to nucleic acid molecules or polypeptides described herein; which have a stimulatory or inhibitory effect on, for example, expression or activity of the nucleic acid molecules or polypeptides of the invention; or which change (e.g., enhance or inhibit) the ability of the polypeptides of the invention to interact with BMP2 binding agents (e.g., receptors).

In one embodiment, the invention provides assays for screening candidate or test agents that bind to or modulate the activity of polypeptides described herein (or biologically active portion(s) thereof). The test agents can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer Drug Des.*, 12:145).

In one embodiment, to identify agents which alter the activity of an BMP2 polypeptide, a cell, cell lysate, or solution containing or expressing an BMP2 polypeptide (e.g., SEQ ID NO:2), or an active fragment or derivative thereof (as described above), can be contacted with an agent to be tested; alternatively, the polypeptide can be contacted directly with the agent to be tested. The level (amount) of BMP2 activity is assessed, and is compared with the level of activity in a control (i.e., the level of activity of the BMP2 polypeptide or active fragment or derivative thereof in the absence of the agent to be tested). If the level of the activity in the presence of the agent differs, by an amount that is statistically significant, from the level of the activity in the absence of the agent, then the agent is an agent that alters the activity of BMP2 polypeptide. An increase in the level of BMP2 activity relative to a control, indicates that the agent is an agent that enhances (is an agonist of) BMP2 activity. Similarly, a decrease in the level of BMP2 activity relative to a control, indicates that the agent is an agent that inhibits (is an antagonist of) BMP2 activity. In another embodiment, the level of activity of an BMP2 polypeptide or derivative or fragment thereof in the presence of the agent to be tested, is compared with a control level that has previously been established. A level of the activity in the presence of the agent that differs from the control level by an amount that is statistically significant indicates that the agent alters BMP2 activity.

The present invention also relates to an assay for identifying agents which alter the expression of BMP2. For example, a cell, cell lysate, or solution containing a nucleic acid encoding BMP2 polypeptide (e.g., BMP2) can be contacted with an agent to be tested. The level and/or pattern of BMP2 expression (e.g., the level and/or pattern of mRNA or of protein expressed) is assessed, and is compared with the level and/or pattern of expression in a control (i.e., the level and/or pattern of the BMP2 expression in the absence of the agent to be tested). If the level and/or pattern in the presence of the agent differs, by an amount or in a manner that is statistically significant, from the level and/or pattern in the absence of the agent, then the agent is an agent that alters the expression of BMP2. Enhancement of BMP2 expression indicates that the agent is an agonist of BMP2 activity. Similarly, inhibition of BMP2 expression indicates that the agent is an antagonist of BMP2 activity. In another embodiment, the level and/or pattern of an BMP2 polypeptide in the presence of the agent to be tested, is compared with a control level and/or pattern that has previously been established. A level and/or pattern in the presence of the agent that differs from the control level and/or pattern by an amount or in a manner that is statistically significant indicates that the agent alters BMP2 expression.

In other embodiments of the invention, assays can be used to assess the impact of a test agent on the activity of a polypeptide in relation to a BMP2 binding partner. For example, a cell that expresses a compound that interacts with BMP2 (herein referred to as a "BMP2 binding partner", which can be a polypeptide or other molecule that interacts with BMP2, such as a receptor) is contacted with BMP2 in the presence of a test agent, and the ability of the test agent to alter the interaction between BMP2 and the BMP2 binding partner is determined. Alternatively, a cell lysate or a solution containing the BMP2 binding partner, can be used. An agent which binds to BMP2 or the BMP2 binding partner can alter the interaction by interfering with, or enhancing the ability of BMP2 to bind to, associate with, or otherwise interact with the BMP2 binding partner. Determining the ability of the test agent to bind to BMP2 or an BMP2 binding partner can be accomplished, for example, by coupling the test agent with a radioisotope or enzymatic label such that binding of the test agent to the polypeptide can be determined by detecting the labeled with $^{125}$I, $^{35}$S, $^{14}$C, or $^{3}$H, either directly or indirectly, and the radioisotope detected by direct counting of radioemmission or by scintillation counting. Alternatively, test agents can be enzymatically labeled with, for example, horseradish peroxidase, alkaline phosphatase, or luciferase, and the enzymatic label detected by determination of conversion of an appropriate substrate to product. It is also within the scope of this invention to determine the ability of a test agent to interact with the polypeptide without the labeling of any of the interactants. For example, a microphysiometer can be used to detect the interaction of a test agent with BMP2 or an BMP2 binding partner without the labeling of either the test agent, BMP2, or the BMP2 binding partner. McConnell, H. M. et al. (1992) *Science*, 257:1906–1912. As used herein, a "microphysiometer" (e.g., Cytosensor™) is an analytical instrument that measures the rate at which a cell acidifies its environment using a light-addressable potentiometric sensor (LAPS). Changes in this acidification rate can be used as an indicator of the interaction between ligand and polypeptide. See the Examples Section for a discussion of know BMP2 binding partners. Thus, these receptors can be used to screen for compounds that are BMP2 receptor agonists for use in treating osteoporosis or BMP2 receptor antagonists for studying osteoporosis. The linkage data provided herein, for the first time, provides such correction to osteoporosis. Drugs could be designed to regulate BMP2 receptor activation which in turn can be used to regulate signaling pathways and transcription events of genes downstream, such as Cbfa1.

In more than one embodiment of the above assay methods of the present invention, it may be desirable to immobilize either BMP2, the BMP2 binding partner, or other components of the assay on a solid support, in order to facilitate separation of complexed from uncomplexed forms of one or both of the polypeptides, as well as to accommodate automation of the assay. Binding of a test agent to the polypeptide, or interaction of the polypeptide with a binding partner in the presence and absence of a test agent, can be accomplished in any vessel suitable for containing the reactants. Examples of such vessels include microtitre plates, test tubes, and micro-centrifuge tubes. In one embodiment, a fusion protein (e.g., a glutathione-S-transferase fusion protein) can be provided which adds a domain that allows BMP2 or an BMP2 binding agent to be bound to a matrix or other solid support.

In another embodiment, modulators of expression of nucleic acid molecules of the invention are identified in a method wherein a cell, cell lysate, or solution containing a nucleic acid encoding BMP2 is contacted with a test agent and the expression of appropriate mRNA or polypeptide in the cell, cell lysate, or solution, is determined. The level of expression of appropriate mRNA or polypeptide in the presence of the test agent is compared to the level of expression of mRNA or polypeptide in the absence of the test agent. The test agent can then be identified as a modulator of expression based on this comparison. For example, when expression of mRNA or polypeptide is greater (statistically significantly greater) in the presence of the test agent than in its absence, the test agent is identified as a stimulator or enhancer of the mRNA or polypeptide expression. Alternatively, when expression of the mRNA or polypeptide is less (statistically significantly less) in the presence of the test agent than in its absence, the test agent is identified as an inhibitor of the mRNA or polypeptide expression. The level of mRNA or polypeptide expression in the cells can be determined by methods described herein for detecting mRNA or polypeptide.

This invention further pertains to novel agents identified by the above-described screening assays. Accordingly, it is within the scope of this invention to further use an agent identified as described herein in an appropriate animal model. For example, an agent identified as described herein (e.g., a test agent that is a modulating agent, an antisense nucleic acid molecule, a specific antibody, or a polypeptide-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

PHARMACEUTICAL COMPOSITIONS

The present invention also pertains to pharmaceutical compositions comprising nucleic acids described herein, particularly nucleotides encoding the polypeptides described herein; comprising polypeptides described herein (e.g., one or more of SEQ ID NO:2); and/or comprising the agent that alters (e.g., enhances or inhibits) BMP2 polypeptide activity described herein. For instance, a polypeptide, protein, fragment, fusion protein or prodrug thereof, or a nucleotide or nucleic acid construct (vector) comprising a nucleotide of the present invention, or an agent that alters BMP2 polypeptide activity, can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active agents.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

Methods of introduction of these compositions include, but are not limited to, intradermal, intramuscular, intraperitoneal, intraocular, intravenous, subcutaneous, topical, oral and intranasal. Other suitable methods of introduction can also include gene therapy (as described below), rechargeable or biodegradable devices, particle acceleration devises ("gene guns") and slow release polymeric devices. The pharmaceutical compositions of this invention can also be administered as part of a combinatorial therapy with other agents.

The composition can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

For topical application, nonsprayable forms, viscous to semi-solid or solid forms comprising a carrier compatible with topical application and having a dynamic viscosity preferably greater than water, can be employed. Suitable formulations include but are not limited to solutions, suspensions, emulsions, creams, ointments, powders, enemas, lotions, sols, liniments, salves, aerosols, etc., which are, if desired, sterilized or mixed with auxiliary agents, e.g., preservatives, stabilizers, wetting agents, buffers or salts for influencing osmotic pressure, etc. The agent may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

Agents described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The agents are administered in a therapeutically effective amount. The amount of agents which will be therapeutically effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the formulation will also depend on the route of administration, and the seriousness of the symptoms of osteoporosis, and should be decided according to the judgment of a practitioner and each patient's circumstances. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the agents can be separated, mixed together in any combination, present in a single vial or tablet. Agents assembled in a blister pack or other dispensing means is preferred. For the purpose of this invention, unit dosage is intended to mean a dosage that is dependent on the individual pharmacodynamics of each agent and administered in FDA approved dosages in standard time courses.

METHODS OF THERAPY

The present invention also pertains to methods of treatment (prophylactic and/or therapeutic) for osteoporosis, using an BMP2 therapeutic agent. An "BMP2 therapeutic agent" is an agent that alters (e.g., enhances or inhibits) BMP2 polypeptide activity and/or BMP2 expression, as described herein (e.g., an BMP2 agonist or antagonist).

The therapy is designed to inhibit, replace or supplement activity of an BMP2 polypeptide in an individual (for example, by administering a nucleic acid encoding an BMP2 polypeptide or a derivative or active fragment thereof including BMP2 from normal individuals not having osteoporosis; by administering an BMP2 polypeptide(s) or a derivative or active fragment thereof including BMP2 from normal individuals not having osteoporosis, or by administering a different splicing variant of the BMP2 polypeptide (s) or a derivative or active fragment thereof; and/or by administering an agent that alters the activity of the BMP2 polypeptide). The BMP2 therapeutic agent can be a nucleic acid (e.g., a gene, cDNA, mRNA, a nucleic acid encoding an BMP2 polypeptide or active fragment or derivative thereof, or an oligonucleotide); a protein, polypeptide, peptide, or peptidomimetic (e.g., an BMP2 polypeptide, such as SEQ ID NO:2, or an active fragment or derivative thereof), an antibody (e.g., an antibody to a mutant BMP2 polypeptide, or an antibody to a non-mutant BMP2 polypeptide, as described above); a ribozyme; a small molecule or other agent that alters BMP2 polypeptide activity and/or gene expression (e.g., which upregulate or downregulate expression of BMP2). More than one BMP2 therapeutic agents can be used concurrently, if desired.

The BMP2 therapeutic agent(s) are administered in a therapeutically effective amount (i.e., an amount that is sufficient to treat the disease, such as by ameliorating symptoms associated with the disease, preventing or delaying the onset of the disease, and/or also lessening the severity or frequency of symptoms of the disease). The amount which will be therapeutically effective in the treatment of a particular individual's disorder or condition will depend on the symptoms and severity of the disease, and can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of a practitioner and each patient's circumstances. Effective doses may be extrapolated from dose-response curves derived from in vitro or animal model test systems.

In one embodiment of the invention, a nucleic acid is used in the treatment of osteoporosis. The term, "treatment" as used herein, refers not only to ameliorating symptoms associated with the disease, but also preventing or delaying the onset of the disease, and also lessening the severity or frequency of symptoms of the disease. In one embodiment, a nucleic acid of the invention (e.g., a nucleic acid encoding an BMP2 polypeptide, such as SEQ ID NO: 1; or another nucleic acid that encodes an BMP2 polypeptide or a splicing variant, derivative or fragment thereof) can be used, either alone or in a pharmaceutical composition as described above. For example, BMP2 or a cDNA encoding the BMP2 polypeptide, either by itself or included within a vector, can be introduced into cells (either in vitro or in vivo) such that the cells produce native BMP2 polypeptide. If necessary, cells that have been transformed with the gene or cDNA or a vector comprising the gene or cDNA can be introduced (or re-introduced) into an individual affected with the disease. Thus, cells which, in nature, lack native BMP2 expression and activity, or have mutant BMP2 expression and activity, or have expression of a disease-associated BMP2 polypeptide variant, can be engineered to express BMP2 polypeptide or an active fragment of the BMP2 polypeptide (or a different variant of BMP2 polypeptide). In a preferred embodiment, nucleic acid encoding the BMP2 polypeptide, or an active fragment or derivative thereof, can be introduced into an expression vector, such as a viral vector, and the vector can be introduced into appropriate cells which lack native BMP2 expression in an animal. In such methods, a cell population can be engineered to inducibly or constitutively express active BMP2 polypeptide. Other gene transfer systems, including viral and nonviral transfer systems, can be used. Alternatively, nonviral gene transfer methods, such as calcium phosphate coprecipitation, mechanical techniques (e.g., microinjection); membrane fusion-mediated transfer via liposomes; or direct DNA uptake, can also be used.

Alternatively, in another embodiment of the invention, a nucleic acid of the invention; a nucleic acid complementary to a nucleic acid of the invention; or a portion of such a nucleic acid (e.g., an oligonucleotide as described below), can be used in "antisense" therapy, in which a nucleic acid (e.g., an oligonucleotide) which specifically hybridizes to the mRNA and/or genomic DNA of BMP2 is administered or generated in situ. The antisense nucleic acid that specifically hybridizes to the mRNA and/or DNA inhibits expression of the BMP2 polypeptide, e.g., by inhibiting translation and/or transcription. Binding of the antisense nucleic acid can be by conventional base pair complementarity, or, for example, in the case of binding to DNA duplexes, through specific interaction in the major groove of the double helix.

An antisense construct of the present invention can be delivered, for example, as an expression plasmid as described above. When the plasmid is transcribed in the cell, it produces RNA which is complementary to a portion of the mRNA and/or DNA which encodes BMP2 polypeptide. Alternatively, the antisense construct can be an oligonucleotide probe which is generated ex vivo and introduced into cells; it then inhibits expression by hybridizing with the mRNA and/or genomic DNA of BMP2. In one embodiment, the oligonucleotide probes are modified oligonucleotides which are resistant to endogenous nucleases, e.g. exonucleases and/or endonucleases, thereby rendering them stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy are also described, for example, by Van der Krol et al. ((1988) *Biotechniques* 6:958–976); and Stein et al. ((1988) *Cancer Res* 48:2659–2668). With respect to antisense DNA, oligodeoxyribonucleotides derived from the translation initiation site, e.g. between the −10 and +10 regions of BMP2 sequence, are preferred.

To perform antisense therapy, oligonucleotides (mRNA, cDNA or DNA) are designed that are complementary to mRNA encoding BMP2. The antisense oligonucleotides bind to BMP2 mRNA transcripts and prevent translation. Absolute complementarity, although preferred, is not required. a sequence "complementary" to a portion of an RNA, as referred to herein, indicates that a sequence has sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid, as described in detail above. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures.

The oligonucleotides used in antisense therapy can be DNA, RNA, or chimeric mixtures or derivatives or modified versions thereof, single-stranded or double-stranded. The oligonucleotides can be modified at the base moiety, sugar moiety, or phosphate backbone, for example, to improve stability of the molecule, hybridization, etc. The oligonucleotides can include other appended groups such as peptides (e.g. for targeting host cell receptors in vivo), or agents facilitating transport across the cell membrane (see, e.g., Letsinger et al. (1989) *Proc. Natl. Acad. Sci. USA* 86:6553–6556; Lemaitre et al., (1987), *Proc. Natl. Acad. Sci. USA* 84:648–652; PCT International Publication No. W088/09810) or the blood-brain barrier (see, e.g., PCT International Publication No. W089/10134), or hybridization-triggered cleavage agents (see, e.g., Krol et al. (1988) *BioTechniques* 6:958–976) or intercalating agents. (See, e.g., Zon, (1988), *Pharm. Res.* 5:539–549). To this end, the oligonucleotide may be conjugated to another molecule (e.g., a peptide, hybridization triggered cross-linking agent, transport agent, hybridization-triggered cleavage agent).

The antisense molecules are delivered to cells which express BMP2 in vivo. A number of methods can be used for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically. Alternatively, in a preferred embodiment, a recombinant DNA construct is utilized in which the antisense oligonucleotide is placed under the control of a strong promoter (e.g., pol III or pol II). The use of such a construct to transfect target cells in the patient results in the transcription of sufficient amounts of single stranded RNAs that will form complementary base pairs with the endogenous BMP2 transcripts and thereby prevent translation of the BMP2 mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art and described above. For example, a plasmid, cosmid, YAC or viral vector can be used to prepare the recombinant DNA construct which can be introduced directly into the tissue site. Alternatively, viral vectors can be used which selectively infect the desired tissue, in which case administration may be accomplished by another route (e.g., systematically).

Endogenous BMP2 expression can also be reduced by inactivating or "knocking out" BMP2 or its promoter using targeted homologous recombination (e.g., see Smithies et al. (1985) *Nature* 317:230–234; Thomas & Capecchi (1987) *Cell* 51:503–512; Thompson et al. (1989) *Cell* 5:313–321). For example, a mutant, non-functional BMP2 (or a completely unrelated DNA sequence) flanked by DNA homologous to the endogenous BMP2 (either the coding regions or regulatory regions of BMP2) can be used, with or without a selectable marker and/or a negative selectable marker, to transfect cells that express BMP2 in vivo. Insertion of the DNA construct, via targeted homologous recombination, results in inactivation of BMP2. The recombinant DNA constructs can be directly administered or targeted to the required site in vivo using appropriate vectors, as described above. Alternatively, expression of non-mutant BMP2 can be increased using a similar method: targeted homologous recombination can be used to insert a DNA construct comprising a non-mutant, functional BMP2 (e.g., a gene having SEQ ID NO: 1), or a portion thereof, in place of a mutant BMP2 in the cell, as described above. In another embodiment, targeted homologous recombination can be used to insert a DNA construct comprising a nucleic acid that encodes an BMP2 polypeptide variant that differs from that present in the cell.

Alternatively, endogenous BMP2 expression can be reduced by targeting deoxyribonucleotide sequences complementary to the regulatory region of BMP2 (i.e., the BMP2 promoter and/or enhancers) to form triple helical structures that prevent transcription of BMP2 in target cells in the body. (See generally, Helene, C. (1991) *Anticancer Drug Des.*, 6(6):569–84; Helene, C., et al. (1992) *Ann, N.Y. Acad. Sci.*, 660:27–36; and Maher, L. J. (1992) *Bioassays* 14(12):807–15). Likewise, the antisense constructs described herein, by antagonizing the normal biological activity of one of the BMP2 proteins, can be used in the manipulation of tissue, e.g. tissue differentiation, both in vivo and for ex vivo tissue cultures. Furthermore, the anti-sense techniques (e.g. microinjection of antisense molecules, or transfection with plasmids whose transcripts are anti-sense with regard to an BMP2 mRNA or gene sequence) can be used to investigate role of BMP2 in developmental events, as well as the normal cellular function of BMP2 in adult tissue. Such techniques can be utilized in cell culture, but can also be used in the creation of transgenic animals.

In yet another embodiment of the invention, polypeptides and/or agents that alter (e.g., enhance or inhibit) BMP2 polypeptide activity, as described herein, can be used in the treatment or prevention of osteoporosis. The polypeptides or agents can be delivered in a composition, as described above, or by themselves. They can be administered systemically, or can be targeted to a particular tissue. The polypeptides and/or agents can be produced by a variety of means, including chemical synthesis; recombinant production; in vivo production (e.g., a transgenic animal, such as U.S. Pat. No. 4,873,316 to Meade et al.), for example, and can be isolated using standard means such as those described herein.

A combination of any of the above methods of treatment (e.g., administration of non-mutant BMP2 polypeptide in conjunction with antisense therapy targeting mutant BMP2 mRNA; or administration of a first variant of BMP2 polypeptide in conjunction with antisense therapy targeting nucleic acid encoding a second variant of BMP2 polypeptide), can also be used.

The invention will be further described by the following non-limiting examples. The teachings of all publications cited herein are incorporated herein by reference in their entirety.

EXEMPLIFICATION

Identification of the BMP2 Gene With Linkage to Osteoporosis

Phenotype and Family Construction

Patients who have low impact fractures and/or take bisphosphonates for treating osteoporosis are automatically treated as affecteds. People with low bone mass density (BMD) measurements are considered to be osteoporotic, and have been shown to have substantially increased risk of fractures. BMD measurements are taken for both the hip and the spine. For each person with BMD measurements, a standardized BMD score is computed (mean 0, standard deviation 1 for the population), which is adjusted for sex, age, body weight and hormone replacement therapy (HRT). For the combined analysis, the two measurements are summed. Population BMD data from Iceland and the United States are used for standardization and adjustment. For example, a person with a positive BMD score is above average and one with a negative score is below average for his/her age, body weight and possibly HRT. Assuming approximate normality, a score of −1 corresponds approximately to the lower $16^{th}$ percentile, etc.

For analysis, we start with a current list of primary people, people who have BMD measurements and/or are severely affected, and for whom we have genotypes. We then use the genealogy database to create family clusters linking these primary people using a threshold distance of 5 meiotic events. This procedure produced 190 potentially informative clusters with a total of 1215 primary people.

Linkage data

Four genome wide scans (GWS) were performed using osteoporotic phenotypes at different skeletal sites; the hip, the spine, and combined phenotypes. All GWS analysis located at 20 cM region on Chr20, between 10 cM and 30 cM based on the Marshfield map.

All of the analyses were performed using the Allegro linkage program developed at deCODE (Gudbjartsson et al., *Nature Genetics*, 25: 12–13, May 2000). The allele sharing analysis uses the Spairs scoring function of GENEHUNTER (Kruglyak et al., *Am. J. Hum. Genet.*, 46: 1347–1363, 1996), but families were weighted using a scheme which is a compromise between weighting families equally and weighting affected pairs equally. The allele-sharing LOD scores were computed using the 'exponential model' described in Kong and Cox, *Am. J. Hum. Genet.*, 61: 1179–1188 (1997).

Hip

The phenotype used was age, sex, weight and HRT corrected BMD<−1 SD at the hip (total hip). Hip fracture cases and bisphosphonate users are also considered affected even if values are above −1 SD. A total of 346 affected were used in this analysis. The GWS resulted in a LOD score of 3.1 using our standard set of markers. Adding 10 extra markers at the region on interest, between 11 cM and 39 cM, resulted in a LOD score of 3.3.

Spine The phenotype was age, sex, weight and HRT corrected BMD<−1 SD at lumbar spine (L2–L4). Vertebral compression fracture cases and bisphosponate users are also considered affected even if values are above −1SD. A total of 402 affected people were used in this analysis. The GWS resulted in a LOD score of 2.4 at the same location as in the hip analysis using the standard set of markers, but a LOD score of 2.9 with the extra marker set.

Combined

The phenotype used was the sum of corrected BMD<−1.5 SD. Vertebral compression fracture, hip fracture, other osteoporosis related low impact fracture (at least two fractures) and bisphosphonate users (BMD measurements before treatment start are used if available) are all considered affected. A total of 522 affected were used in this analysis. The GWS resulted in a LOD score of 2.5 with the standard marker set, but a LOD score of 3.9 using the extra markers in the region.

Combined Severe

The phenotype used was the sum of the age, sex, weight and HRT corrected BMD<−2.3 SD. Vertebral compression fracture, hip fracture, other osteoporosis related low impact fracture (at least two fractures) and bisphosphonate users affected. The number of affected in this analysis was 290. The GWS resulted in a LOD score of 3.8 with the standard set but a LOD score of 4.7 was reached using the extra 10 markers in addition.

Corticosteroid users and women with early menopause were excluded as affected in all analysis.

The BMP2 Gene

The BMP2 gene is located in this region. Only 5 kb are between the marker D20S846, which gives the highest LOD score, and the 3' end of the gene. The gene has been sequenced and characterized in terms of exon/intron structures, promoter region and transcriptional start sites. This information are publicly available.

A number of nucleotide changes are observed in the Icelandic population. These changes have not to our knowledge been described before, as follows:

Promoter Region:
   A to G at nucleotide position 420;
   A to G at nucleotide position 472;
   G to C at nucleotide position 1464;
   G to A at nucleotide position 1722;
   C to G at nucleotide position 1914;
Coding Region:
   T to G at nucleotide position 3747; resulting in an amino acid change from serine to alanine at amino acid position 37;
   A to G at nucleotide position 3899; no amino acid change;
   G to T at nucleotide position 3918; resulting in an amino acid change from alanine to serine at amino acid position 94;
   A to T at nucleotide position 11980; resulting in an amino acid change from arginine to serine at amino acid position 189;
3' UTR and Downstream Region:
   C to T at nucleotide position 12571;
   T to C at nucleotide position 13066;
   A to G at nucleotide position 13209;
   C to A at nucleotide position 13296; and
at least one deletion in nucleotides at positions 13533–13536 (all numbering is relative to SEQ ID NO: 1).

BMP2 binds to the receptors BMPR-IA or BMPR-IB, and BMPR-II, leading to formation of receptor complex heterodimer and phosphorylation of the BMPR-IA or BMPR-IB receptors. Once activated, these receptors subsequently phosphorylate SMAD1, SMAD5 or SMAD8, which in turn form complexes with SMAD4 and translocate to the nucleus where the transcription of specific genes is affected (Massague, J., *Annu. Rev. Biochem.*, 67:753–791 (1998); Chen, D. et al., *J. Cell Biol.*, 142(1):295–305 (1998)). SMADs 6 and 7 block signals by preventing the activation of SMAD1, SMAD5 or SMAD8 by the BMP2 receptors and have been shown to inhibit osteoblast differentiation (Miyazono, K., *Bone*, 25(I):91–93 (1999); Fujii, M., et al., *Mol. Biol. Cell*, 1(11):3801–3813 (1999)). BMP2 stimulates Cbfa1, alkaline phosphatase and Collagen type I (osteoblast specific proteins) expression through BMPR-IB (Chen, D. et al., *J. Cell Biol.*, 142(1):295–305 (1998). Cbfa1 regulates the expression of osteoprotegerin (OPG), which is an osteoblast-secreted glycoprotein that functions as a potent inhibitor of osteoblast differentiation and thus of bone resorption (Thirunavukkarasu, K., et al., *J. Biol. Chem.*, (2000). Cbfa1 controls osteoblast differentiation and bone formation. During cellular aging of human osteoblasts, there is a significant reduction (up to 50%) of Cbfa1 mRNA (Christiansen, M., et al., *J. Gerontol. A Biol. Sci. Med. Sci.*, 55(4):B194–200 (2000).

Frequency of the nucleotide changes at positions 3747, 3899 and 11980 relative to SEQ ID NO 1 found in the coding region of the gene BMP2 in the Icelandic population.

Affected-unrelated: are all unrelated patients with the combined phenotype. Most also have the hip and spine phenotype.

Controls-unrelated: are all unrelated controls, affected status unknown. Fam_aff: are affected in our familial material, divided into different phenotypes as appropriate.

No difference in frequency of the nucleotide changes is observed between the affected-unrelated and fam_affected.

A→G transition at nucleotide position 3899 in SEQ ID NO: 1 does not affect the amino acid composition.

Wt/wtwt/GG/Gtotalaffected-unrelated186551134Controls-unrealted 166345124fam_aff_combined258167173fam_aff_hip176456137fam_aff_spine227255149

A→T transversion at nucleotide position 11980 in SEQ ID NO: 1, changing the amino acid arginine to serine.

wt/wtwt/TT/totalaffected-unrelated216750138controls-unrelated 167150137fam_aff_hip145139104fam_aff_spine18513910

T→G transversion at nucleotide position 3747 in SEQ ID NO: 1, changing the amino acid serine to alanine.

Wt/wtwt/GG/Gtotalaffected-unrelated128100138controls-unrelated25470267fam_aff_combined275190294fam_aff_spine238180256

Of the 10 affected-unrelated that are wt/G, 9 also have the spine phenotype and 8 have the hip phenotype.

Results and Discussion

As a result of the linkage studies, the analysis shows that this locus is involved in multiple osteoporosis phenotypes. Furthermore, mutation within the human BMP2 gene is likely to explain the phenotypes in these families. Sporadic occurrence of osteoporosis, i.e., occurrence without familial connection, can also be determined using the information contained herein.

Osteoporosis could be caused by a defect in the BMP2 gene as follows: A mutation in the BMP2 gene (transcription, splice, protein variant etc.) could lead to a reduction of it's action on Cbfa1 through BMPR-IB and the subsequent signaling pathway, that would lead to less bone formation because of fewer and less active osteoblasts and more bone resorption because of less OPG and more osteoclasts. This would lead to bone loss. Since a significant reduction of Cbfa1 levels is associated with aging osteoblasts, this effect could become more important with older age.

While this invention has been particularly shown and described with reference to preferred embodiments thereof, it will be understood by those skilled in the art that various changes in form and details may be made therein without departing from the spirit and scope of the invention as defined by the appended claims.

TABLE 1

```
LOCUS         __ 14759 bp  DNA
DEFINITION    Human bone morphogenetic protein 2 (SEQ ID NO:2)
              (BMP2) gene, complete cds (SEQ ID NO:1),
              complete sequence.
KEYWORDS      .
SOURCE        human.
ORGANISM      Homo sapiens
              Eukaryota; Metazoa; Chordata; Craniata; Vertebrata;
              Mammalia; Eutheria; Primates; Catarrhini; Hominidae; Homo.
REFERENCE     1 (bases 1-14759)
AUTHORS       Blakey, S.
TITLE         Direct Submission
JOURNAL       Submitted (04-APR-2000) Sanger Centre, Hinxton,
              Cambridgeshire, CB10 1SA, UK. E-mail enquiries:
              humquery@sanger.ac.uk Clone requests:
              clonerequest@sanger.ac.uk
COMMENT       This sequence was taken from GenBank sequence AL035668
              (VERSION AL035668.15, GI:4995292), bp 118501 . . . 133259.
FEATURES      Location/Qualifiers
     source        1 . . . 14759
                   /organism="Homo sapiens"
                   /db_xref="taxon: 9606"
                   /chromosome="20"
                   /map="20p12"
                   /clone="RP5-859D4"
                   /clone_lib="RPCI-5"
     gene          2072 . . . 12634
                   /gene="BMP2"
                   /note="BMP2A"
                   /db_xref="LocusID:650"
                   /db_xref="MIM:112261"
     exon          2072 . . . 2387
                   /gene="BMP2"
                   /number=1
     exon          3632 . . . 3984
                   /gene="BMP2"
                   /number=2
     CDS           /join(3639 . . . 3984, 11757 . . . 12601)
                   /gene="BMP2
                   /note="BMP2 exons defined by comparison to mRNA
                   sequence (NM_001200)
                   /codon_start=1
                   /product="bone morphogenetic protein 2 precursor"
                   /protein id="NP_001191.1"
                   /db_xref="GI:4557369"
```

/translation="MVAGTRCLLALLLPQVLLGGAAGLVPELGRRKFAAASSGRPSSQ

PSDEVLSEFELRLLSMFGLKQRPTPSRDAVVPPYMLDLYRRHSGQPGSPAPDHRLERA

ASRANTVRSFHHEESLEELPETSGKTTRRFFFNLSSIPTEEFITSAELQVFREQMQDA

LGNNSSFHHRINIYEIIKPATANSKFPVTRLLDTRLVNQNASRWESFDVTPAVMRWTA

QGHANHGFVVEVAHLEEKQGVSKRHVRISRSLHQDEHSWSQIRPLLVTFGHDGKGHPL

HKREKRQAKHKQRKRLKSSCKRHPLYVDFSDVGWNDWIVAPPGYHAFYCHGECPFPLA

DHLNSTNHAIVQTLVNSVNSKIPKACCVPTELSAISMLYLDENEKVVLKNYQDMVVEG

```
                   CGCR"
     exon          11757 . . . 12634
                   /gene="BMP2"
                   /number=3
BASE COUNT      3913 a   3147 c   3351 g   4348 t
```

CCTTGGTTTTGGGGATCATTTGGGCAAGCCCGAGGTGCTGTGCATGGGGCTCCTGGAAT

CCTGGGAAGGGCAGAAAGCCTTGGCCCCAGACTCATCGTGCAGCAGCTCTGAGCAGTATT

TCGGCTGAGGAGTGACTTCAGTGAATATTCAGCTGAGGAGTGACTTGGCCACGTGTCACA

GCCCTACTTCTTGGGGCCTGGTGGAAGAGGGTGGCGTAGAAGGTTCCAAGGTCCCAAAC

TGGAATTGTCCTGTATGCTTGGTTCACACAGTGCGTTATTTTACCTTCCTCTGAGCTGCT

AATCGCCTGCCTCTGAGCTGGGTGAGATAAATATCACAAGGCACAAAGTGATTGTACAAT

TABLE 1-continued

```
AAAAAAATCAAATCCCTCCCATCCATCCTTCAGTCTGCCACACACGCAGTCTACGTTACA
CACATGTCACGTAAAGCAGGATGACATCCATGTCACATACATAGACATATTAACCGAAAT
GTGGCCCTTCGGTTGCATATATTCTCATACATGAATATATTTATAGAAATATATGCACAT
ATTTTTGTATATTGGATATATTTATGTAACTATAAATTTACATGCGTATGGATATGAAAA
TAAATGCATACACATTTATGTAAAAAAATTTGTACACATGCATTTACATATGTAAATACA
TACATCTCTATGTATTAATGTTTAAAAACACTCAATTTCCAGCCTGCTGTTTTCTTTTAA
TTTTCCTCCTATTCCGGGGAAACAGAAGCGTGGATCCCACGTCTATGCTATGCCAAAATA
CGCTGTAATTGAGGTGTTTTGTTTTGTTTTGTTTTTTGAAATCGTATATTACCGAAAAAC
TTCAAACTGAAAGTTGAATAACGGGCCCAGCGGGGAAATAAGAGGCCAGACCCTGACCCT
GCATTTGTCCTGGATTTCGCCTCCAGAGTCCCCGCGAGGGTCCGGCGCGCCAGCTGATCT
CTCCTTTGAGAGCAGGGAGTGGAGGCGCGAGCGCCCCCTTGGCGGCCGCGCGCCCCGC
CCTCCGCCCCACCCCGCCGCGGCTGCCCGGGCGCGCCGTCCACACCCCTGCGCGCAGCTC
CCGCCCGCTCGGGGATCCCCGGCGAGCCGCGCCGCGAAGGGGAGGTGTTCGGCCGCGGC
CGGGAGGGAGCCGGCAGGCGGCGTCCCCTTTAAAAGCCGCGAGCGCCGCGCCACGGCGCC
GCCGCCGCCGTCGCCGCCGCCGGAGTCCTCGCCCCGCCGCGCTGCGCCCGGCTCGCGCTG
CGCTAGTCGCTCCGCTTCCCACACCCCGCCGGGGACTGGCAGCCGCCGCCGCACATCTGC
CGCCACAGCCTCCGCCGGCTACCCGAACGTTCTCGGGGCCAGCGCCGAGTGGATCACCGG
GGACCGCGAGGCACCCGCGCGCCGCAGACCCCGCGCGGGCTGGAGCACCCGGCAGAGCGC
GCCACAGCGCCGTGGCCTCTGCTGCCCGGGCTGCGCCAGAGCCGCGGACGGGCGCGCAGA
GCGCCGGGGACTCCGGAGCCGATCCCTAGCGCCGCGATGCGGAGCACCTACTGCAGGAGA
TCGGGGGCCTGGGACGCGCTGGCCGAGGTGTGATCGGACCCCAGGCTAGCCACAAAGGGC
ACTTGGCCCCAGGGCTAGGAGAGCGAGGGGAGAGCACAGCCACCCGCCTCGGCGGCCCGG
GACTCGGCTCGACTCGCCGGAGAATGCGCCCGAGGACGACGGGGCGCCAGAGCCGCGGTG
CTTTCAACTGGCGAGCGCGAATGGGGTGCACTGGAGTAAGGCAGAGTGATGCGGGGGGG
CAACTCGCCTGGCACCGAGATCGCCGCCGTGCCCTTCCCTGGACCCGGCGTCGCCCAGGA
TGGCTGCCCCGAGCCATGGGCCGCGGCGGAGCTAGCGCGGAGCGCCCGACCCTCGACCCC
CGAGTCCCGGAGCCGGCCCCGCGCGGGGCCACGCGTCCCTCGGGCGCTGGTTCCTAAGGA
GGACGACAGCACCAGCTTCTCCTTTCTCCCTTCCCTTCCCTGCCCCGCACTCCTCCCCCT
GCTCGCTGTTGTTGTGTGTCAGCACTTGGCTGGGGACTTCTTGAACTTGCAGGGAGAATA
ACTTGCGCACCCCACTTTGCGCCGGTGCCTTTGCCCCAGCGGAGCCTGCTTCGCCATCTC
CGAGCCCCACCGCCCCTCCACTCCTCGGCCTTGCCCGACACTGAGACGCTGTTCCCAGCG
TGAAAAGAGAGACTGCGCGGCCGGCACCCGGGAGAAGGAGGAGGCAAAGAAAAGGAACGG
ACATTCGGTCCTTGCGCCAGGTCCTTTGACCAGAGTTTTTCCATGTGGACGCTCTTTCAA
TGGACGTGTCCCCGCGTGCTTCTTAGACGGACTGCGGTCTCCTAAAGGTAGAGGACGCGG
GCCAGGGCCCGGGGTGGGTGGTGGGTGGGAGGGGGATTTGGGCAGCCACTGCGGTAGAGC
CCTTCCTTACGTCCAGGCCAGAAGTAAACAGACCCCTCTCCAGT&CACGTGCAACGGAGC
CCTGCAGGGGCTCCCACTTCCAGCTGCCCCGGGCGACCGTAAGCCTCACCCTCCCGGCCC
GCACTCTTCCACCCCTCTTTCTTCCCCTCTCCCTGGAATACTTTTGGAGCTGTTAACACT
TAGATGAGGTGTTTTATTTATTTATTTATTTTTAATTTTTTAAAAACTTTTTGG
GTCAAAGAAATCCCTTTGAGAGGGTAGCCCCTGGGTTTCACCCGTTAGCTGAGAACCTGT
```

TABLE 1-continued

CCGCTCTGCCATGGTGATCTCCATTCTTCAAGTGTTTCCGGGAGACTTGGTTTCTTTGCT

CAGAGCCGTGTCCCATTTAGGAAAGTACTAGGAGTTTGGGGTTCTCCCTACTTGTTTCCA

GAAATGCGAGGGGTCAGTACTGAAGGATCACTTGGTACTGTGTTTTTAACAGCTGACACG

TGCATTAATAGATATTCACCATTTACGTAATCCCGGGAAGATACATGTGTATCTTGACTG

CACTGTGGGGATGCGGGATGGAGCTGCCTTTCGAGACACCCCTGAGGGTAGGGGCCTGGG

ACACAAGTCATAAGTGGCTTCAGAAGTTGTGGCCTTGAGCTTACAGGGTCTGGAAGCTAT

AAGGGTGTGTGTGTGTGTGTGTGTGTGTGTGTGTGTCAGGAAGTTCTATACAGTGC

CTCTAAGGAAGTCACATGCACCATTTATGTGTGTTTATATGCCAGACAGCGCTCAGCACT

CCGCATTTGGGTTTGTATAGGGGACGCAGGGTGTCAGATCAAGCGGTGGTTTTCCCAGGT

TCCCGGCATTGGCTGTCAGCGCTGTGTCACACACAAAAAAGTGACAGTCATTGGCGCTGG

TTTGGTTGGGGGGGAGGGCAAATCCCAAATCTGATGTCAGACGAGCTAAGCGTTGGATGG

GAGCGATAAATCATCTGGTTCAGGAACTTGGGACCCTTCATTATCCCAAACGTTTGAGCT

TCGGTCGGTCTTACCTAGACTCGTGAGTGTGCCAAGCCAGGAGGGCATCCTGGAGGAGGC

ACGCCAGCCAAATGGGAGACCGGGCCGCGGGGCGCGAGGGGGAGGACTGGGCGGGGAA

CTCGGGTGACTCACGTCGGTCCTGTCCGCAGGTCGACCATGGTGGCCGGGACCCGCTGTC

TTCTAGCGTTGCTGCTTCCCCAGGTCCTCCTGGGCGGCGCGGCTGGCCTCGTTCCGGAGC

TGGGCCGCAGGAAGTTCGCGGCGGCGTCGTCGGGCCGCCCCTCATCCCAGCCCTCTGACG

AGGTCCTGAGCGAGTTCGAGTTGCGGCTGCTCAGCATGTTCGGCCTGAAACAGAGACCCA

CCCCCAGCAGGGACGCCGTGGTGCCCCCCTACATGCTAGACCTGTATCGCAGGCACTCAG

GTCAGCCGGGCTCACCCGCCCCAGACCACCGGTTGGAGAGGGCAGCCAGCCGAGCCAACA

CTGTGCGCAGCTTCCACCATGAAGGTGAGGCATGGAGCAGGGCGTGGGGCGGGGAGTCA

CCCTGCAAAGCCCTCCACCGTGGGCAGACTGCAGCCGTCCCTGTAGAGGCAGCTTGGCCG

GGGCACCAGCGGACGTTTCCACTCTTGCTTCTGTACTATCGTTTCTGAATCTGATTTTAA

CTCACTGCTTGTGTGGTGGGGGAGCCAGGGATTCCCCTTTAGTAACTCCGCACCCTCTTC

CTGGCTTGCAGCCAGAAGAGCTACTCCTCCTGGAAGAATTGGAGAGAAATCAAGTGATGG

GGAAGATGAGGGCAAAAGGCATGCCTCTAGTCAGCTAAACGTGCAAGAATTCCACAGAGG

GAAAAGGAGAAAAAGGGAGGCAGATTGAGATTTCTTTAAGTCTGTTTGGAAGCTTTTGCT

CTATAAATCTGCCGCTTAAGCCAGGGTTTTAGGGTAGACAGAGCCAAGGGCAGAGTTTTC

AGAGATAGTATTGAAAAATCAAAGCCCAGGGCCCCAAAGTCTTTCTAATTTATAGTTGAT

CTGGGCCTGGTTTGGAAGATTTTGAATCCCAATCTAATCCCCGTGGGAGATCAATACTAC

AATCAATCTTATTGTTTCCACAATGACTTTCTTGTCCTGTGCTTAAATCTGAGATAGGCT

CTGAGTAGAGACAAGGCAAGCCTTCAGATAAAAGCGTTTGTAGCAGCTGCCTGTTTTTTT

TTCATGTGCACCGAAATGTGGATTTTTTTTCTTTTATGATACTACATGTGGTTTTTCTA

AGGTGGGATATTTCTGCTTGTTTCATCAGAAGGGCATTTAGTGGACTGGAAATGTCTTAC

AGCAGCTATTGAGGTCTGCTGTACCTAAGTTCTTAGAGCAATTAGTCAAAAATATGTTCC

ACTTCAATTCTTTTTCTACACTTTTAAATGCTTCTTTGGCTTAATACATTTAAAATAGAG

CATGGGTTTCTTCAATTCCTAGAAAAGAGTACAAAAGTGTATATCACAGAGCAACCACTT

GGCAGATATTTGGGGAGTTGGGAGTGAAGTTCTCTTTCTTGCCTTTCCCTGCTTAGGTGG

TAAATTTCAAGTGGGAAATTTACACTGATAATAGACTAATGGGAAATGGCACTTCCAGAT

TABLE 1-continued

```
GTTTTCTCCCAGTGTGAAGGGTGACTTATACTTGTGAGAGTATTTGTTGGTAATGGGAAT
AAGTCCCAAAGGCAAGCCACATAGCAGAAGATACGTTCTCATTGAGGCAGCTACACATTA
CGACGGGACACTGAATTGATCATCAGTTCATTTACAAGCACATTTCTAAGTGAGGTGCT
CTCTGCTAGCAGAAATCAGATTTGAAAGGCAGTAAGATCTCACTCCACTCTTTCAGAATT
CATCCAATGAAAGCAGAAATCACCTGTTGTCATATGTAAAATTTGTGTGTATGTGTACAT
TCTGCCATCTTAACCCTGAAATGATTATAGATCCAGCTAATCATTCCCAGGTAATGCTGA
TTAGAATACTTTTTTTTTTGTATAGGAATGTAATAAGAACAACTGTTTTAGACACCTCTT
CTGGAAATTTAGCATGGAAGCTCTCAACTTTATTTTTAAGGCCTGGAAGATGCTGTGTCT
CTGTTACAACTTAAAAGGAAGATCATTTAAGTTAGTTAACACCTAAAACATTCCATTGTG
TGAGGATTTTATCAGTGATGTCTGCATATTCTCATCATTCATCTAGAAGTGGTTTGATCA
GAACTAAACAGGCTACACGTTATTCAACTGTGTTATTTTAACTTAAAAAGCATGCTTGAG
TTTATAAAATCAGAATTTATATCTTTGTGAGTGTAAATGTTACCTGAGAAACAGTACAGA
AGTGACCAACTTGATTAAAATCAACTTGTAATAACTTCAGGTCTTAATGCAGTTAGATAA
TGGAGAAAAGCTATGTAATTTTGCCCCAAATTTCAACTAATCCATTTCTTGTCTCATTAT
GACTAATATATCATCCTTAATCTGGATGGATATAGCACTTTTTTCAAGACTAATCATTGT
TGTATACACCCAGGATTTGCTTTTGATAAACATCCTTGTGCCATGCATGCCACGAAAAAA
GTTTTTGGTAAACCATGTGATGAAGGTTGCTGGCTCAAGAACAGAATTTAGTTTCTACAG
CATTAATGAGCATTTATTTGAAAAAAGACCATAAAGACCCAATCATAAGAATTACCTGTT
GGGTTTTCTTTGTAGGTGTGATCGAATGGTTTGGTGGAATTACTCGACGAGATATCATGA
TAGCATTCTTTCAACCAATATGAGTATAATGCGACCATATCATAGGGGATCTGAGACAGA
ATTATCAGTTGTATTTTTCCTATTGAATTTTGTCTAGTCCTTTCTCCAGTGGCTTTTATT
TGGGAGAATATCAGCTTTGCTAAAATGTTATTGTTTTCAAGATCATTAAAAAGTGCTTCA
GCTACATAGACCTTTGGAAACTGCCATTGAACATAGAAAAGTCAGTTCTGCAAGTGGAAA
GAGTGTTTTGTGTATTGCTGTAGTTGGAAACACATTGAAACTGGTTGACTTCACTGGCCC
TCCAAAAAGTCTTTATGCTTTTTTGTCAGATGGGAGAGAGAAAGACCAGGTGCTTCTTGT
TCTCCTCACTCTGAAGGACACAGTCTTCTTTCTACATGAAATAACTGGATTATTTGCCTC
TGTGACTGAAGCTTTCAAATAGAGATTAACCCTCTTTCCACAAATATAATTATTATGAAA
ATATCCATATAATAGAAAAGTTCAAGAAATAACTATTGCCCTGCATTAGAGACTTTGTGG
CACAAATTCCCCCGTGCAAACAACAGATTTGGACACATAGATCCACCAAAACCAATACTT
ACCTGGTATGGTTCCCTAGTGGCCCCAGGTATTTCATTGTCATTACAGAGGCCACATTAA
GTAGGAAAATTACTCTATTTGGAAATGGTTGTTGAGATTGAGGCTTTGGTGTCCAGTGAT
ACTTCCTTGGCACTGACATTTTCCGTTCCACCTGTTTTTTAGTGGTTCCCCTAAATTTCT
CTTAATCCCTTTGCAGTGAACTATTTTGCGTTCTTAGACTTGCTCTTTGTGTATTTTCAC
TGAGACAATAAGAGAATATTTCATCATTCCGAAGGTGTTGGTGTTAAGGGTGGGCAGAGG
CCAAATCAGGGTTGTTGATGACAACCATGCTCTCTATTCCTTTATTTGCCATTCCCTTGT
TGTATTTTTTTAAAATGGAATGTTTTAACCTTTTGTATTTGATATTTTTTTCTCCTT
GATCAGTTGTCTGTTATTTTATTATCTGGAAAATCTTATATTATACTCAGCCTCTTTCAT
TTTGTGTTAGGGCAGTGACTTCCAGCCTTACTGATTGCCAGCATATCCCCAGGTTTTGTT
GTTGTTGTTGTTGTTTTACTGGAGATTTTTTAGCCCAAAGTGTGTTTTAAAATCCTCGAA
GCATAACGGTAACTTACTTTTTTGATAAAACTTACCATACTTTATTTAGAACAAAAGGGC
```

TABLE 1-continued

```
AGCCACAAAATAGCAGTGGCTCCTTATAAAATAGACACATTCCAGTGGGCCCCGTCACTT

TTCTGCTCATTTCTGTCTGTTCTGTCCATCATACCTAAGTCATATATTTCTGTTCATTTA

GTTGGGACAGAACTCACCCAATGTTATCATTGTACTAAATATAAATGTGCCCCTAATGGT

TTTGACTTTTGCTTAAGTTTTTGAGTCCTCATGTATGTTAGGTAGTGCCATCTAGTAGCC

AGAAATTTGGGAACTGGCTGGGCATGATGGCTAATACCTGTAATCCCAGCACTTTGGGAG

GCTTAGGTGGGTGGATCACTTGAGGTCAGGAGTTCCAGACCAGCCTGGCCAACATGGTGA

AACCACATCTCTACTAAAATATAAAAAAATAGCCAGGTATGATGGCCCATGCCTGTAATC

CGAGCTAATTGGGAGGCTGAGATGGGAGGACTGCTTGAACCTGGGAGGTGGAGGCTGCTG

TGAGCCAAGATTGTGCCACTGCACTCCAGCCTGGGCAACAGAGTGAGACCCTGTGTCACA

AAAACAAGAAACAAAACAAAACAAAAGACAAGAAACCTGAGAAGCGCAGTAGATTCAATT

ATATATATCTACTTTTAATTTGCTAGCTCTGTGACCTTAGGAAAGTTACATAACCTCTCT

GAACTGCAACTGTTTCATTTACAAAATGGAGATAATGATAGTTTTTCTCTAATTGGTTTG

TTGTGAGATAATTCATATAAAGCTGATGGTGCCAGATTACACTCAAAAAAAGCATTCAGC

TGTCATTATCATTATGACTTCTTTTGTTAATGTTATAGCCTTTCCTTCTCTAGGGAAAAG

GAGGCCAGAGTGGACCTAGGCTGACTGAGAGAATTCAGCTCAGTCTTTTGAATTATTTTG

AGGTAGAGGAATGATTGATATAGTATAGATTATTAAATTAGGACTTCACTTTTGGAGAAA

AGTTCAGATATCATTGTTGTCTTATTTTTCTTCACTTTCCCACATTTTTGCAGCCATAGC

TCCATCCATTTGGTTAAGAACTTAGAAGCTCACAAACTCGGGTCAAAGACAGGTCGAAAT

CCTCAAATCCCTTAAGAACTTCAGCTTATTCAGGAAGGGATATTTACAGAAAACTAGCAA

TTGTATAAGTCTCCAAAAAAGCATACATTACTTGAGGATCCATATATTTTGGCATCCTC

AGGGTTGCTGTGATGATTTATAGAAGGTTTGTTTATTTAATTTACTTTATTTCAAATAGG

TTTTAATTTTTGTACCCTTAAGAAAAGATTCGTACTCTTCCCTGGCAGATTAAAGAAAAT

GAGCGTATATTCCCTAACCTTGGCCAGTTACTTTCCTGGGTTTGAGGGTTTCTGTGAACG

TCTAACTTACCTCTGTGACCTGTTTCTGCAACCAGGGGTGTTGCAATGGATGCTTTTGTC

TTGAGGATGGGACCTTTCAAGAAACAGATTCACTGAGGTGCAGTGGGAAGGTCAGAGAAA

GATCTTCGTATCGCCTATTATTATTTGCTCGTCTATTTTTTCTCCTTTCTTAAGGCCACT

AACTGATTCTCCTTTGCTAAGGCTGCCTACTTCCACTGAGACCTTGAACCACATGAAATT

GTTGTTGTCTGTGTTTCTGGTCAAATAGTGGCAATTTTGTATGATTCAATCTTGTCATTT

AATTTTTTGGGAGGTTATTATTCTATTTCATACCTTTTTTATACCCATCTTCTTTACTTC

ATTTACCTGTCCCTCATACTTGACTTGTAGCTTGTCCCTTCACTGTCATCGTCTGGCCAT

GTGGGTGTACGTGTCTGCGACAGAGAGAATGTGTGAGAATGTATCTTTCTTTATGCAT

TGGGATTTAGGGTTTTTCTTGCAATTGTGATTTCTCTGGGCACTTTTGTTAATATAGCTA

GTCAGCGAGTGCTCTAGATAATTTTCCTTGCCTCCCCCTCTTTGAAAGAAAAGAGGGTGT

TCTTAGATGTATTCTTATCAGATAAGCCAGTAGCTCAGGTGCTGGTCTGGCTTTGGTGTC

ATTGGGGTCTGAGGTTGCTGACTTTTACCTTCTCTGCTGAAAAATTACCTTCAGCAGAAA

CGTCTGAATTGCAAGGAGAAGGAGAAAAAAACAGGCCAAACACAGTCCTTGGTACTCCTT

GGGAGCCACTGAGAAGAGTCCAGGTTCAAATGGTCAGAAGGTTATTTTAATGATTGTGTC

TGGCCTAAAGTACCATTAGCTTCCAGTGGAGTTTAGAATGTGGATGGATCCTGAAAGGTA

TTCCCCAGAGGTTTGGATTAATAGGCACAAGGGAACCCTAAAGGACTCTATTGGCCTGAT
```

TABLE 1-continued

```
ACTCCCCATATCCACGTAGAAGAGCTTTAGAAGAACCTTCTGTTCTGAGACCCTGGCTGG
GCCCACCCAGAGCTGGCCCATTCAACTCTTACTCCTTTGCCACCACTAATGGTTCTTCTA
CTAGTTTTTATATTATTTAACAAAAAGGCACTTTAAAAATGCACTCCTGGCAATCTATAC
TGGAATATGAAAAACATGCTGCAAAACCTTGACACTCCAAGTGTGGTCTTACAGTTCCCA
GAATCCCCTCCTTGAGGAGCTGCTAGAAATGCTGAATCTCAAGCATCTCCCCAGACCTAC
TGAATCAGAGCCTGCATCTGAAGCTTTACGGTGTACAAGCTGTTTTATGTGAAGGCTGAA
GTTTGAAAAGCACTGCATTAAAGCGTTAGTTTGGTATAAACTGCCCTGACTGAACTTGGT
GTGTCCACTTAGCTTGCATGATGACTGTTGCTTTGATGATGAAGGCTTACACGGGTAGAT
CCTTTGAGTGAGTGATCTGACATGATTCTCCTTTGCTAAGGCATCTAGATTCAGTGCACA
ACTTACAGCTGTTTGTCTTTAGGGGAAATACAACTGTAAAATTAATAAAAACATAGTCTC
TTCTTATGATAACATGGAACGATGGCAAAATAGATTTTGTTAGCACTTGGGTAGGAATTC
TGAATGAAGCAGGCAAATTCTGTTGGCAGTGAAATGATAGGATGTGGTAAAGTTAGAATA
AAATAAACTTAAATGTCTCAAACTCTCATGGTATATACTACCAGTTTAATAATAATGTTG
TACCTTTGATGATTTGCAGACTACAAGCATTCAAGGTGCTGTGTTATATATTACTTGCTT
GGAGAATAATACTTCTTAAAAATTGAAATTCAGAAATTTTAAATCAGACAAAGCTTTTGT
GCATGGCCCACTTAAATGGCTATTTTGAAATAATGATAGTGGATATAGAAGGATTATTCT
GTAATAGGATGAGACTGTTCCTTTTGTCATGGAGATCATAATCATATTTTTGTAAATTTT
TATTATTTTTTGGTTTTGTGTCCATCCTGCACACTATTACTGGGTAGGTACATGGTTTT
TTAACATGGTTTATCTTTCAAAACTATAAAGGCATTGCAAACAGAAGACAGGTCATTTAT
TTTTCTTCCAAAAGCATCTAAAATGAGATTTTGATATTTGAGGTCATAAAGAGGTGAGAG
AACAGACAACAGTTGGGAAAGCTATTTCTCTTGAAATTGTTTGGCCTTAATTACTACAGT
GTCCTAGTACCACCCATACGTTTCCAAAGAAGTAGATCCCTGTAAATGCCTTTGTCTCTG
GACTTTTGAGTAAAATAGTAGGGTGTGCTTTGCAAAATGTCATCGTTGATGTTGAGTTTC
AGAGTCTTTAATTAGGAAGCTGAAATCTGTATATCGAGATTTGTAAATCATCTAAATTGC
AGAGTAATGTTTTAGAATACTGCTTAAGGGATTGGCATTAAAGCCTTTTTTAAAAAGAA
ATGCAATAATTTCCTCAAATCCTCACTCATTAGACCTCTACTAACTATAGTGCTGACTTT
TTTTTTTTTTTACCCTAAAGTCTGGAATTCCAAAGAAATGCTTCACCATTTCCCCCATTA
TTATAGCCACCTGGAAGCAGTATTCATGTATTAGATCAAAAACACAACAAAGAATTATGA
AAGGTTGTTTCCTGGTATGCAATGCATGATGACATGAACTTACAGAACAGAGAGAAGGGA
GGCTCCATGTTTATTTAAAGAGGAAATTTTTATTTTCTGGTTACCTACTTTTACATGGGT
TACATCAAATCCCACGATGAGGTTTAAAAATTCTCATAGATAATCAAACGTCATTACTTG
GCTTACTGAAATTCAGACTTTTCTTTTTTCTTCCCTGTTTTTCTCTATCAAATTAGAATC
TTTGGAAGAACTACCAGAAACGAGTGGGAAAACAACCCGGAGATTCTTCTTTAATTTAAG
TTCTATCCCCACGGAGGAGTTTATCACCTCAGCAGAGCTTCAGGTTTTCCGAGAACAGAT
GCAAGATGCTTTAGGAAACAATAGCAGTTTCCATCACCGAATTAATATTTATGAAATCAT
AAAACCTGCAACAGCCAACTCGAAATTCCCCGTGACCAGACTTTTGGACACCAGGTTGGT
GAATCAGAATGCAAGCAGGTGGGAAAGTTTTGATGTCACCCCCGCTGTGATGCGGTGGAC
TGCACAGGGACACGCCAACCATGGATTCGTGGTGGAAGTGGCCCACTTGGAGGAGAAACA
AGGTGTCTCCAAGAGACATGTTAGGATAAGCAGGTCTTTGCACCAAGATGAACACAGCTG
GTCACAGATAAGGCCATTGCTAGTAACTTTTGGCCATGATGGAAAAGGGCATCCTCTCCA
```

TABLE 1-continued

```
CAAAAGAGAAAAACGTCAAGCCAAACACAAACAGCGGAAACGCCTTAAGTCCAGCTGTAA
GAGACACCCTTTGTACGTGGACTTCAGTGACGTGGGGTGGAATGACTGGATTGTGGCTCC
CCCGGGGTATCACGCCTTTTACTGCCACGGAGAATGCCCTTTTCCTCTGGCTGATCATCT
GAACTCCACTAATCATGCCATTGTTCAGACGTTGGTCAACTCTGTTAACTCTAAGATTCC
TAAGGCATGCTGTGTCCCGACAGAACTCAGTGCTATCTCGATGCTGTACCTTGACGAGAA
TGAAAAGGTTGTATTAAAGAACTATCAGGACATGGTTGTGGAGGGTTGTGGGTGTCGCTA
GTACAGCAAAATTAAATACATAAATATATATATATATATATTTTAGAAAAAAGAAAAA
AACAAACAAACAAAAAAACCCCACCCCAGTTGACACTTTAATATTTCCCAATGAAGACTT
TATTTATGGAATGGAATGGAAAAAAAAACAGCTATTTTGAAAATATATTTATATCTACGA
AAAGAAGTTGGGAAAACAAATATTTTAATCAGAGAATTATTCCTTAAAGATTTAAAATGT
ATTTAGTTGTACATTTTATATGGGTTCAACCCCAGCACATGAAGTATAATGGTCAGATTT
ATTTTGTATTTATTTACTATTATAACCACTTTTTAGGAAAAAAATAGCTAATTTGTATTT
ATATGTAATCAAAGAAGTATCGGGTTTGTACATAATTTTCCAAAAATTGTAGTTGTTTT
CAGTTGTGTGTATTTAAGATGAAAAGTCTACATGGAAGGTTACTCTGGCAAAGTGCTTAG
CACGTTTGCTTTTTTGCAGTGCTACTGTTGAGTTCACAAGTTCAAGTCCAGAAAAAAAAA
GTGGATAATCCACTCTGCTGACTTTCAAGATTATTATATTATTCAATTCTCAGGAATGTT
GCAGAGTGATTGTCCAATCCATGAGAATTTACATCCTTATTAGGTGGAATATTTGGATAA
GAACCAGACATTGCTGATCTATTATAGAAACTCTCCTCCTGCCCCTTAATTTACAGAAAG
AATAAAGCAGGATCCATAGAAATAATTAGGAAAACGATGAACCTGCAGGAAAGTGAATGA
TGGTTTGTTGTTCTTCTTTCCTAAATTAGTGATCCCTTCAAAGGGGCTGATCTGGCCAAA
GTATTCAATAAAACGTAAGATTTCTTCATTATTGATATTGTGGTCATATATATTTAAAAT
TGATATCTCGTGGCCCTCATCAAGGGTTGGAAATTTATTTGTGTTTTACCTTTACCTCAT
CTGAGAGCTCTTTATTCTCCAAAGAACCCAGTTTTCTAACTTTTTGCCCAACACGCAGCA
AAATTATGCACATCGTGTTTTCTGCCCACCCTCTGTTCTCTGACCTATCAGCTTGCTTTT
CTTTCCAAGGTTGTGTGTTTGAACACATTTCTCCAAATGTTAAACCTATTTCAGATAATA
AATATCAAATCTCTGGCATTTCATTCTATAAAGTCCAACCTGTAAGAGAAAATGGTGCAT
TTGTATAGCGCTTACAATGATGACCTTGTGTTTGCATTTTTGTTTCTGAAGTTATATATT
TTAGAGGGGTGGGGAAAGGTAATGAATGGCTGGAAAATTGCAGGCAAGTTATTTGATA
AGTCATATTTGCACTAAAGGTGTTACCAGTGATTTAGTATTTTTCAAATGAACTTCTTTG
GGGCAGAAAGATTTAAGGGAAAACTAAAGCCTACAAAACAAGCAAAACCTGGATAACCCG
AGATAAAGTTTCAGAGATAATAGCCCATGCAACAGAGGCAACGGTGCCAGAAAATTAGAA
AGGGAAAGTGTCGGAGATCAGCTTCTATAAGAACATCTGCCAGTTGGACTGACGCCCAAA
CAGAATGAAGTCAAATTAGGCTGCTCAGATTGAACACTTACCAGAGTGTCAGGGCTTCTG
TACCCTGGGTTAGAATCAGACCAAGGAAGGGTTCAGCAGATGTTCATAAGAGCAGGGCAC
CCACAACTACCCACTATTTTACTGGCAGTATTTTAGGTCAGTTTCCAGGACTTTGCATCC
CCTCTGATCCTGCCATGCATGATTGGTGAAACCTACCTCTAATCTCCTTGGAATTGGCTA
AAAAACAGTGTGTTTATAATGGAACAGACTGTTATAATCAAATTCTTCCTAGGAATTAAC
TTTTGATGACTATGAGCTTAGTTACAGTTCGGAGGTTATGAGGTTATGTAAACCTTATCT
TTAAATGTGCATGACAGTTATCTTTTACTAATGCTGGTTAACTTTTAAAATCTTGCAGCT
```

TABLE 1-continued

```
CCTTTTTATCTCTAGTTCTATTGTTCTTGATTAGGTGAGAACCATTAGATCATACCCAAC

TGAGGGGATTGGGGTCTTGTTTGTTCTCCAGCTGTTCTTCACCCTCTATTGCCATGGACA

TGAAGGACAGACTGCACGGTCTTAACATGTTAAAACGAATGACCCATGTTTTCTCATAT
```

What is claimed is:

1. A method of diagnosing a susceptibility to osteoporosis in an individual, comprising detecting a polymorphism in a human BMP2 gene of SEQ ID NO: 1, wherein the presence of a "T" at nucleotide position 11980 is indicative of a susceptibility to osteoporosis, compared with an individual having an "A" at nucleotide position 11980.

2. A method of diagnosing a susceptibility to osteoporosis in an individual, comprising detecting a polymorphism in a human BMP2 gene of SEQ ID NO: 1, wherein the polymorphism is selected from the group consisting of A to G at nucleotide position 420; A to G at nucleotide position 472; G to C at nucleotide position 1464; G to A at nucleotide position 1722; C to G at nucleotide position 1914; T to G at nucleotide position 3747; A to G at nucleotide position 3899; G to T at nucleotide position 3918; A to T at nucleotide position 11980; C to T at nucleotide position 12571; T to C at nucleotide position 13066; A to G at nucleotide position 13209; C to A at nucleotide position 13296; at least one deletion in nucleotides at positions 13533–13536 and combinations thereof.

3. A method of diagnosing a susceptibility to osteoporosis in an individual, comprising detecting a polymorphism in a human BMP2 gene of SEQ ID NO: 1, wherein the presence of a "G" at nucleotide position 3747 is indicative of susceptibility to osteoporosis compared to an individual having a "T" at nucleotide position 3747.

4. The method of claim 1, wherein the polymorphism is detected in a sample from a source selected from the group consisting of: blood, serum, cells and tissue.

5. The method of claim 1, wherein detecting the polymorphism is performed by a method selected from the group consisting of: allele-specific hybridization, using oligonucleotide arrays, direct manual sequencing, automated fluorescent sequencing, single-stranded conformation polymorphism assays, clamped denaturing gel electrophoresis, denaturing gradient gel electrophoresis, mobility shift analysis, restriction enzyme analysis, heteroduplex analysis, chemical mismatch cleavage, RNase protection assays, use of polypeptides that recognize nucleotide mismatches and allele-specific PCR.

6. The method of claim 2, wherein the polymorphism is detected in a sample from a source selected from the group consisting of: blood, serum, cells and tissue.

7. The method of claim 2, wherein detecting the polymorphism is performed by a method selected from the group consisting of: allele-specific hybridization, using oligonucleotide arrays, direct manual sequencing, automated fluorescent sequencing, single-stranded conformation polymorphism assays, clamped denaturing gel electrophoresis, denaturing gradient gel electrophoresis, mobility shift analysis, restriction enzyme analysis, heteroduplex analysis, chemical mismatch cleavage, RNase protection assays, use of polypeptides that recognize nucleotide mismatches and allele-specific PCR.

8. The method of claim 3, wherein the polymorphism is detected in a sample from a source selected from the group consisting of: blood, serum, cells and tissue.

9. The method of claim 3, wherein detecting the polymorphism is performed by a method selected from the group consisting of: allele-specific hybridization, using oligonucleotide arrays, direct manual sequencing, automated fluorescent sequencing, single-stranded conformation polymorphism assays, clamped denaturing gel electrophoresis, denaturing gradient gel electrophoresis, mobility shift analysis, restriction enzyme analysis, heteroduplex analysis, chemical mismatch cleavage, RNase protection assays, use of polypeptides that recognize nucleotide mismatches and allele-specific PCR.

* * * * *